(12) United States Patent
Shimada

(10) Patent No.: US 11,994,525 B2
(45) Date of Patent: May 28, 2024

(54) MEMBRANE PROTEIN ANALYSIS SUBSTRATE, METHOD OF PRODUCING MEMBRANE PROTEIN ANALYSIS SUBSTRATE, METHOD OF ANALYZING MEMBRANE PROTEIN AND MEMBRANE PROTEIN ANALYSIS GRID

(71) Applicant: KYUSHU UNIVERSITY, NATIONAL UNIVERSITY CORPORATION, Fukuoka (JP)

(72) Inventor: Atsushi Shimada, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 18/193,357

(22) Filed: Mar. 30, 2023

(65) Prior Publication Data
US 2023/0258665 A1    Aug. 17, 2023

Related U.S. Application Data

(63) Continuation of application No. PCT/JP2021/039829, filed on Oct. 28, 2021.

(30) Foreign Application Priority Data

Oct. 28, 2020  (JP) ................. 2020-180734

(51) Int. Cl.
G01N 33/92   (2006.01)
G01N 33/487  (2006.01)

(52) U.S. Cl.
CPC ....... *G01N 33/92* (2013.01); *G01N 33/48721* (2013.01)

(58) Field of Classification Search
None
See application file for complete search history.

(56) References Cited

U.S. PATENT DOCUMENTS

2016/0189919 A1   6/2016  Passmore et al.
2017/0205363 A1   7/2017  De Jonge et al.

FOREIGN PATENT DOCUMENTS

| JP | 2011167609 A | 9/2011 |
|---|---|---|
| JP | 2016532267 A | 10/2016 |
| WO | 2009154688 A1 | 12/2009 |

OTHER PUBLICATIONS

R.G. Efremov, et al., "Architecture and conformational switch mechanism of the ryanodine receptor", Nature, 517(7532): p. 39-43 + extended material, Jan. 2015.*

(Continued)

*Primary Examiner* — J. Christopher Ball
(74) *Attorney, Agent, or Firm* — Dechert LLP; Andrew T. Wilkins

(57) ABSTRACT

A membrane protein analysis substrate including an electron microscope grid having a plurality of through-holes; a lipid bilayer membrane that is provided to cover at least one of the plurality of through-holes; and membrane proteins that are retained in a part planarly overlapping the through-holes of the lipid bilayer membrane, wherein the lipid bilayer membrane has a lipid monolayer, and wherein the lipid monolayer is larger than the through hole in a plan view, adheres to the grid, and constitutes a part of the lipid bilayer membrane.

20 Claims, 17 Drawing Sheets

(56) References Cited

OTHER PUBLICATIONS

I.G. Denisov, et al., "Nanodiscs for structural and functional studies of membrane proteins", Nature Structure & Molecular Biology, 23(6): p. 481-486, Jun. 2016.*
A. Soloaga et al., "Insertion of *Escherichia coli* α-haemolysin in lipid bilayers as a non-transmembrane integral protein: prediction and experiment", Molecular Microbiology, 31(4): p. 1013-1024, Febr. 1999.*
D. Levy, et al., "Two-Dimensional Crystallization on Lipid Layer: A Successful Approach for Membrane Proteins", Journal of Structural Biology, 127(1): p. 44-52, Aug. 1999.*
Notice of Allowance for JP2022-505405 dated Mar. 1, 2022.
PCT International Search Report for PCT/JP2021/039829 dated Dec. 7, 2021.
Faelber et al., "Structure and assembly of the mitochondrial membrane remodelling GTPase Mgm1," Nature. 2019; 571:429-33.
Menny et al., "CryoEM reveals how the complement membrane", Nature Communications. 2018; 9:5316.
Nannenga et al., "Overview of Electron Crystallography of Membrane Proteins," Curr. Protoc. Protein Sci. 2013; 72:17.15.1-17.15.11.
Office Action from Canadian Patent Application No. 3,194,443, dated Jun. 28, 2023 (5 pages).
McAdulff et al., "Incorporation of membrane proteins into lipid bilayers for scanning transmission electron microscopy and single particle reconstruction," Microscopy and Microanalysis 1999 5: 1314-1315.
McAlduff et al., "Freestanding lipid bilayers as substrates for electron cryomicroscopy of integral membrane proteins," J Microsc. 2002 205:113-117.
Office Action from Chinese Patent Application No. 202180064225.1, dated Jul. 18, 2023 (26 pages).
Sumitomo et al., "Confinement of fluorescent probes in microwells on si substrates by sealing with lipid bilayers," Appl Phys Express. 2010 3: 107001.
Levy D et al: "Two-dimensional crystallization of membrane proteins: the lipid layer strategy", FEBS Letters, Elsevier, Amsterdam, NL, vol. 504, No. 3, Aug. 31, 2001 (Aug. 31, 2001), pp. 187-193.
Heymann J Bernard et al: "Electron and atomic force microscopy of membrane proteins", Current Opinion in Structural Biology, vol. 7, No. 4, Aug. 1, 1997 (Aug. 1, 1997), pp. 543-549.
Office Action from EP Patent Application No. 21886325, mailed on Mar. 6, 2024 (18 pages).

\* cited by examiner

MEMBRANE PROTEIN ANALYSIS SUBSTRATE, METHOD OF PRODUCING MEMBRANE PROTEIN ANALYSIS SUBSTRATE, METHOD OF ANALYZING MEMBRANE PROTEIN AND MEMBRANE PROTEIN ANALYSIS GRID

TECHNICAL FIELD

The present invention relates to a membrane protein analysis substrate, a method of producing a membrane protein analysis substrate, a method of analyzing membrane proteins and a membrane protein analysis grid. Priority is claimed on Japanese Patent Application No. 020-180734, filed Oct. 28, 2020, the content of which is incorporated herein by reference.

BACKGROUND ART

Biological membranes in which proteins are embedded are typically "lipid bilayer membranes" composed of two thin phospholipid layers. Examples of conventional methods of forming a planar lipid bilayer membrane include a painting method, a Montal-Mueller method, and a vesicle fusion method (for example, refer to Patent Document 1). As studies on proteins using lipid bilayer membranes many studies on embedding proteins in lipid, bilayer membranes that cover pores of the substrate and functions of ion channels using the embedded proteins have been conducted so far.

CITATION LIST

Patent Document

[Patent Document 1]
Japanese Unexamined Patent Application, First Publication No. 2011-167609

SUMMARY OF INVENTION

Technical Problem

In the field of structural biology, structure analysis of proteins is performed. Particularly, three-dimensional structures of proteins that function while embedded in biological membranes such as cell membranes are considered important in understanding biological reactions and pharmacological activities in which these proteins are involved. Therefore, structure analysis of proteins embedded in biological membranes has high industrial importance for applications such as drug discovery, and researchers are investigating the structures of proteins embedded in biological membranes.

Regarding the above "proteins embedded in biological membranes," hereinafter, proteins that function in the lipid bilayer membrane represented by the biological membrane or on the surface of the lipid bilayer membrane will be referred to as "membrane proteins." The membrane proteins include "integral membrane proteins" that are embedded in the lipid bilayer membrane and "peripheral membrane proteins" that temporarily bind to the surface of the lipid bilayer membrane or temporarily bind to the integral membrane proteins. In addition, the integral membrane proteins include membrane proteins partially embedded in the lipid bilayer membrane and so-called "transmembrane proteins" having a region that spans the lipid bilayer membrane.

A crystal structure analysis method is known as a protein structure analysis method. However, basically, in crystal structure analysis, the structure of membrane proteins present in the lipid bilayer membrane or on the surface of the lipid bilayer membrane is not obtained. Therefore, for structure analysis of membrane, proteins present in the lipid bilayer membrane or on the surface of the lipid bilayer membrane, direct observation using an electron microscope is considered effective without crystallizing the membrane proteins present in the lipid bilayer membrane or on the surface of the lipid bilayer membrane.

As a membrane protein structure analysis method using an electron microscope, a low-temperature electron microscope method (cryo-electron microscope method), which is a type of a technique using a transmission electron microscope, is known. In the low-temperature electron microscope method, thin vitreous ice is prepared in the through-holes of the electron microscope grid, and a sample of membrane proteins trapped and fixed in this ice is observed. As the membrane proteins to be observed, membrane proteins solubilized with a surfactant are known. In addition, as the membrane proteins to be observed, membrane proteins that are embedded in liposomes which are spherical lipid bilayer membranes and nanodisks which are disk-shaped nanostructures are known. Nanodisks are formed by surrounding a phospholipid bilayer membrane with a belt of membrane skeletal proteins.

However, membrane proteins solubilized with a surfactant do not always have three-dimensional structure that is similar to that when they are embedded in the lipid bilayer membrane. In addition, when membrane proteins in liposomes are observed, the thickness of ice required to retain the liposomes is large, and the quality of electron microscope images tends to deteriorate. In addition, when membrane proteins in nanodisks are observed, membrane proteins and membrane protein complexes that are too large to be retained in nanodisks are excluded from observation targets.

In addition, in order to retain membrane proteins in liposomes or nanodisks and perform high resolution analysis, it is required to use a large amount of membrane proteins and prepare a sample having a high concentration. However, since there are many membrane proteins for which a sample having a high concentration cannot be prepared, there is a demand for a technique through which electron microscope images can be acquired even when the concentration, of the membrane protein sample is low and the amount thereof is small.

In addition, particularly, since a complex operation is required to prepare membrane proteins embedded in nanodisks as a sample for electron microscope observation, there is a demand for a technique through which electron microscope images can be acquired more easily than in the related art.

The present invention has been made in view of such circumstances, and an object of the present invention is to provide a novel membrane protein analysis substrate having a lipid bilayer membrane retaining membrane proteins. In addition, an object of the present invention is to provide a method of producing a membrane protein analysis substrate which allows membrane proteins retained in a lipid bilayer membrane to be easily formed in an electron microscope grid. In addition, an object of the present invention is to provide a method of analyzing membrane proteins using a membrane protein analysis substrate. In addition, an object of the present invention is to provide a novel membrane protein analysis grid having a lipid bilayer membrane that covers pores of a supporting membrane of an electron microscope grid.

Solution to Problem

In order to achieve the above objects, one aspect of the present invention includes the following embodiments.

[1] A membrane protein analysis substrate, including:
an electron microscope grid having a plurality of through-holes;
a lipid bilayer membrane that is provided to cover at least one of the plurality of through-holes; and
membrane proteins that are retained in a part planarly overlapping the through-holes of the lipid bilayer membrane,
wherein the lipid bilayer membrane has a lipid monolayer, and
wherein the lipid monolayer is larger than the through-hole in a plan view, adheres to the electron microscope grid, and constitutes a part of the lipid bilayer membrane.

[2] The membrane protein analysis substrate according to [1],
wherein one lipid monolayer constituting the lipid bilayer membrane is formed of a first lipid, and
wherein the other lipid monolayer constituting the lipid bilayer membrane is formed of a second lipid different from the first lipid.

[3] The membrane protein analysis substrate according to [1],
wherein the two lipid monolayers constituting the lipid bilayer membrane are formed of the same lipid.

[4] The membrane protein analysis substrate according to [2] or [3],
wherein the surface of the electron microscope grid is hydrophobic,
wherein one lipid monolayer constituting the lipid bilayer membrane covers a first surface of the electron microscope grid,
wherein the other lipid monolayer constituting the lipid bilayer membrane covers a second surface of the electron microscope grid, and
wherein the one lipid monolayer and the other lipid monolayer are bonded inside the through-hole, form the lipid bilayer membrane, and cover the through-hole.

[5] The membrane protein analysis substrate according to [3],
wherein the surface of the electron microscope grid is hydrophobic,
wherein one lipid monolayer constituting the lipid bilayer membrane covers one surface of the electron microscope grid,
wherein the other lipid monolayer constituting the lipid bilayer membrane is discretely provided inside the plurality of through-holes, and
wherein the one lipid monolayer and the other lipid monolayer are bonded inside the through-hole, form the lipid bilayer membrane, and, cover the through-hole.

[6] The membrane protein analysis substrate according to [2] or [3],
wherein the surface of the electron microscope grid is hydrophilic, and
wherein the lipid bilayer membrane covers the through-hole from one surface of the electron microscope grid.

[7] A method of forming a lipid bilayer membrane of producing a membrane protein analysis substrate, including:
a process of providing a first lipid monolayer on a first surface of an electron microscope, grid having a plurality of through-holes;
a process of providing a second lipid monolayer on a second surface of the electron microscope grid and forming a lipid bilayer membrane in which the first lipid monolayer and the second lipid monolayer are bonded; and
a process of retaining membrane proteins in the lipid bilayer membrane;
wherein, in the process of providing a first lipid monolayer, the plurality of through-holes are covered from the side of the first surface with the first lipid monolayer,
wherein, in the process of forming a lipid bilayer membrane, the plurality of through-holes are covered from the side of the second surface with the second lipid monolayer, and
wherein the first lipid monolayer and the second lipid monolayer are bonded inside, the plurality of through-holes.

[8] The method of producing a membrane protein analysis substrate according to [7],
wherein the process of providing a first lipid monolayer includes bringing the first surface into contact with the first lipid monolayer formed on a liquid surface of a first solution.

[9] The method of producing a membrane protein analysis substrate according to [7] or [8],
wherein the process of providing a second lipid monolayer includes bringing the second surface into contact with the second lipid monolayer formed on a liquid surface of a second solution,

[10] The method of producing a membrane protein analysis substrate according to [9],
wherein, in the process of retaining membrane proteins, the membrane proteins are added to the second solution, and
wherein the membrane proteins move from the second solution to the lipid bilayer membrane and are retained in the lipid bilayer membrane.

[11] The method of producing a membrane protein analysis substrate according to [10],
wherein, in the process of retaining membrane proteins, after the membrane proteins solubilized in a buffer solution with a surfactant are added to the second solution, the surfactant adsorbent is added to the second solution, and the surfactant is removed from the second solution.

[12] A method of producing a membrane protein analysis substrate including:
a process of bringing one surface of an electron microscope grid having a plurality of through-holes into contact with a lipid monolayer formed on a liquid surface of a solution and forming a lipid bilayer membrane inside the plurality of through-holes; and
a process of adding membrane proteins to the solution and retaining the membrane proteins in the lipid bilayer membrane,
wherein, in the process of forming a lipid bilayer membrane, the lipid monolayer is transferred to the one surface, and the plurality of through-holes are covered from the side of the one surface with the lipid monolayer, wherein the lipid monolayer forms a self-assembled lipid bilayer membrane inside the plurality of through-holes, and wherein, in the process of retaining membrane proteins, the membrane proteins move from the solution to the lipid bilayer membrane and are retained in the lipid bilayer membrane.

[13] The method of producing a membrane protein analysis substrate according to [12], wherein, in the process of adding membrane proteins, after the membrane proteins solubilized in a buffer solution with a surfactant are added to the solution the surfactant adsorbent is added to the solution, and the surfactant is removed from the solution.

[14] A method of producing a membrane protein analysis substrate, including:

a process of forming a lipid bilayer membrane retaining membrane proteins; and a process of transferring the lipid bilayer membrane retaining the membrane protein to one surface of an electron microscope grid having a plurality of through-holes, wherein, in the process of transferring to one surface, the lipid bilayer membrane is brought into contact with the one surface in such a manner that it covers the entire through-holes.

[15] A method of analyzing membrane proteins, including a process of observing the membrane proteins retained by the membrane protein analysis substrate according to any one of [1] to [6] or the membrane proteins retained by the membrane protein analysis substrate produced by the method of producing a membrane protein analysis substrate according to any one of [7] to [14] under an electron microscope.

[16] The method of analyzing membrane proteins according to [15], further including a process of staining the membrane proteins retained in the lipid bilayer membrane before the process of observing under an electron microscope.

[17] The method of analyzing membrane proteins according to [15] or [16], wherein, in the observing process, the membrane proteins are observed by a low-temperature electron microscope method.

[18] A membrane protein analysis grid, including:

an electron microscope grid having a plurality of through-holes; and a lipid bilayer membrane that is provided to cover at least one of the plurality of through-holes, wherein one lipid monolayer constituting the lipid bilayer membrane covers a first surface of the electron microscope grid, wherein the other lipid monolayer constituting the lipid bilayer membrane covers a second surface of the electron microscope grid, and wherein the one lipid monolayer and the other lipid monolayer are bonded inside the through-hole, form the lipid bilayer membrane, and cover the through-hole.

[19] The membrane protein analysis grid according to [18], wherein one lipid monolayer constituting the lipid bilayer membrane is formed of a first lipid, and wherein the other lipid monolayer constituting the lipid bilayer membrane is formed of a second lipid different from the first lipid.

[20] The membrane protein analysis grid according to [18], wherein the two lipid monolayers constituting the lipid bilayer membrane are formed of the same lipid.

Advantageous Effects of Invention

According to the present invention, it is possible to provide a novel membrane protein analysis substrate having a lipid bilayer membrane retaining membrane proteins. In addition, it is possible to provide a method of producing a membrane protein analysis substrate which allows membrane proteins retained in a lipid bilayer membrane to be easily formed in an electron microscope grid. In addition, it is possible to provide a method of analyzing membrane proteins using a membrane protein analysis substrate. In addition, it is possible to provide a novel membrane protein analysis grid having a lipid bilayer membrane that covers pores of a supporting membrane of an electron microscope grid.

DESCRIPTION OF EMBODIMENTS

First Embodiment

Hereinafter, a method of producing a membrane protein analysis substrate, a method of analyzing membrane proteins and a membrane protein analysis grid according to a first embodiment will be described with reference to FIG. 1 to FIG. 8. Here, in all the following drawings, sizes, ratios, and the like of respective components are appropriately changed in order for the drawings to be easy to view.

<<Membrane Protein Analysis Substrate and Membrane Protein Analysis Grid>>

FIGS. 1 to 4 are illustrative diagrams showing a membrane protein, analysis substrate 1 and a membrane protein analysis grid 90 according to the present embodiment.

Figure 1:
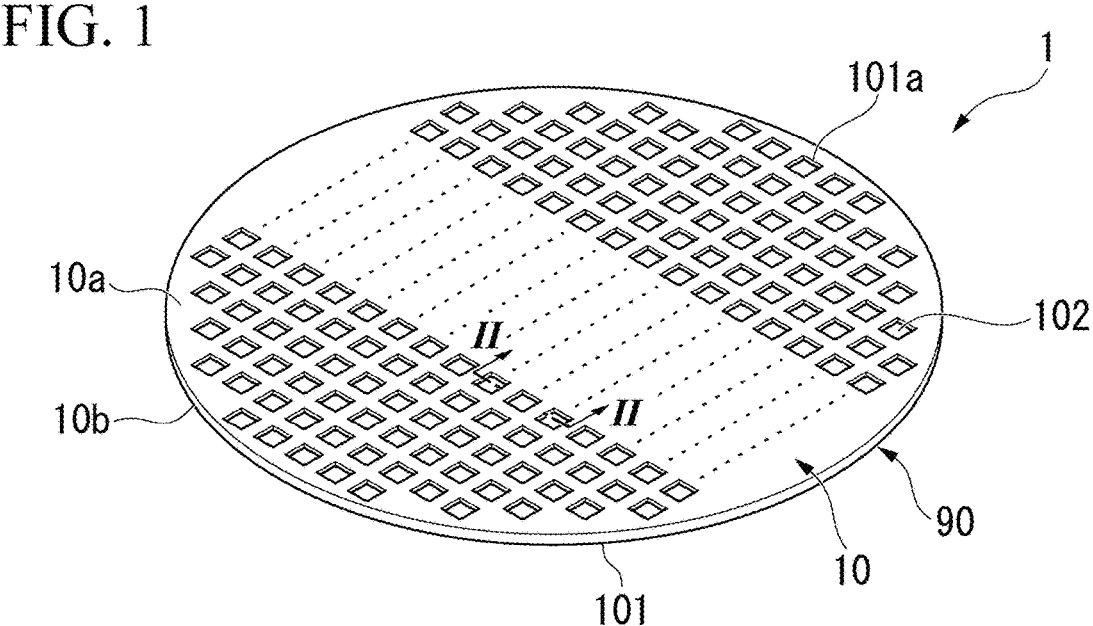
FIG. 1 is an illustrative diagram showing a membrane protein analysis substrate 1 according to a first embodiment.
Figure 2:
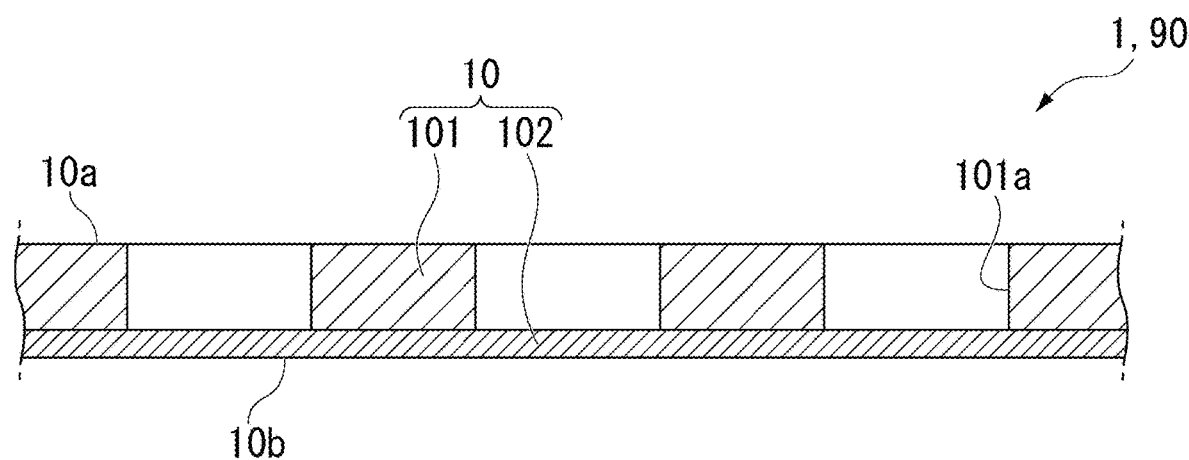
FIG. 2 is an illustrative diagram showing the membrane protein analysis substrate 1 according to the first embodiment.
Figure 3:
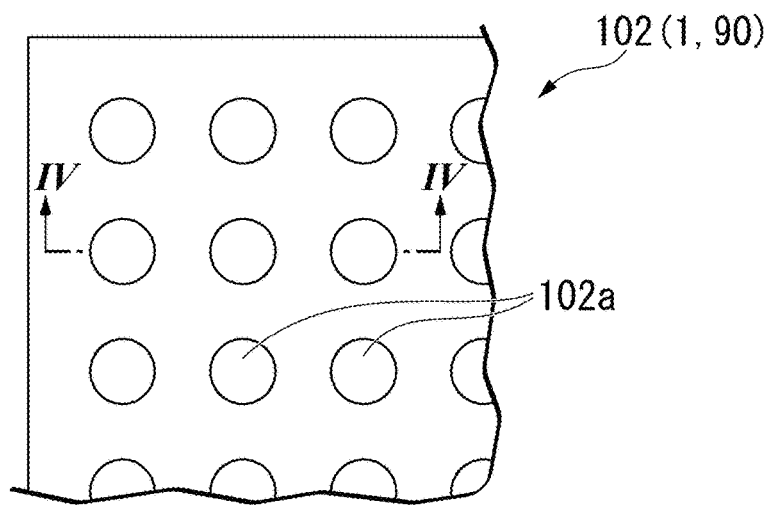
FIG. 3 is an illustrative diagram showing the membrane protein analysis substrate 1 according to the first embodiment.
Figure 4:
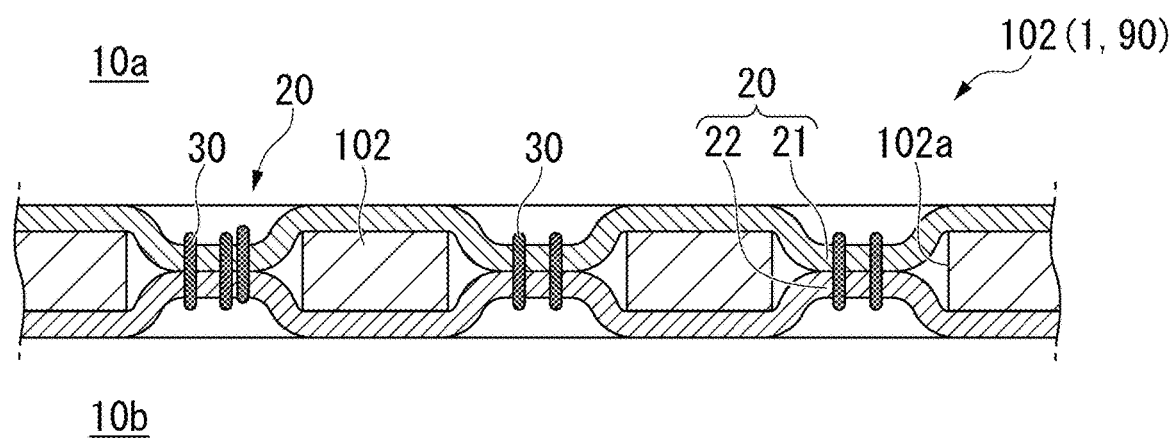
FIG. 4 is an illustrative diagram showing the membrane protein analysis substrate 1 according to the first embodiment.
Figure 5:
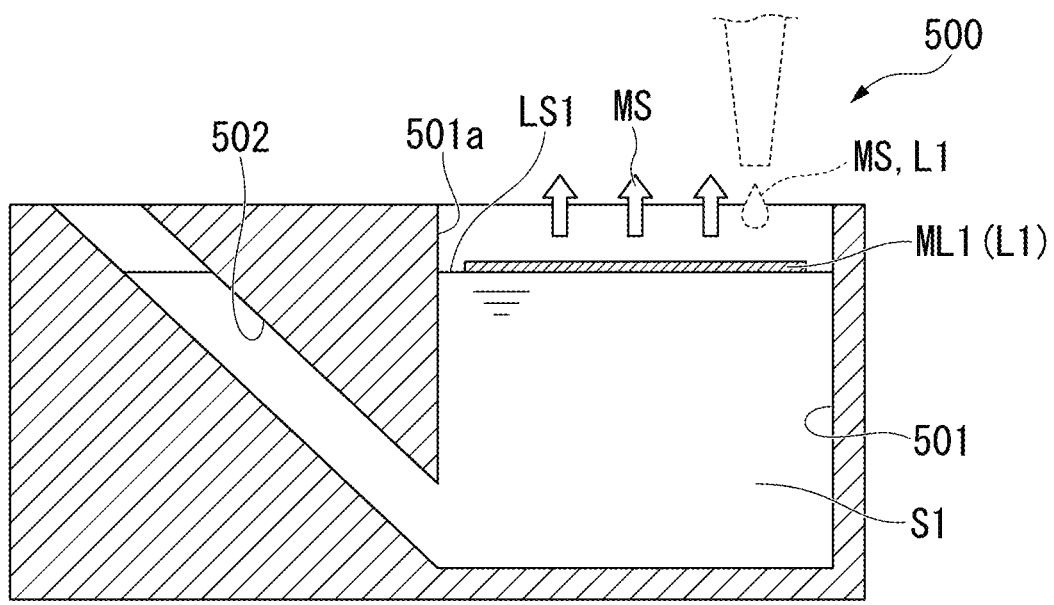
FIG. 5 is an illustrative diagram showing a method of producing a membrane protein analysis substrate according to the first embodiment.
Figure 6:
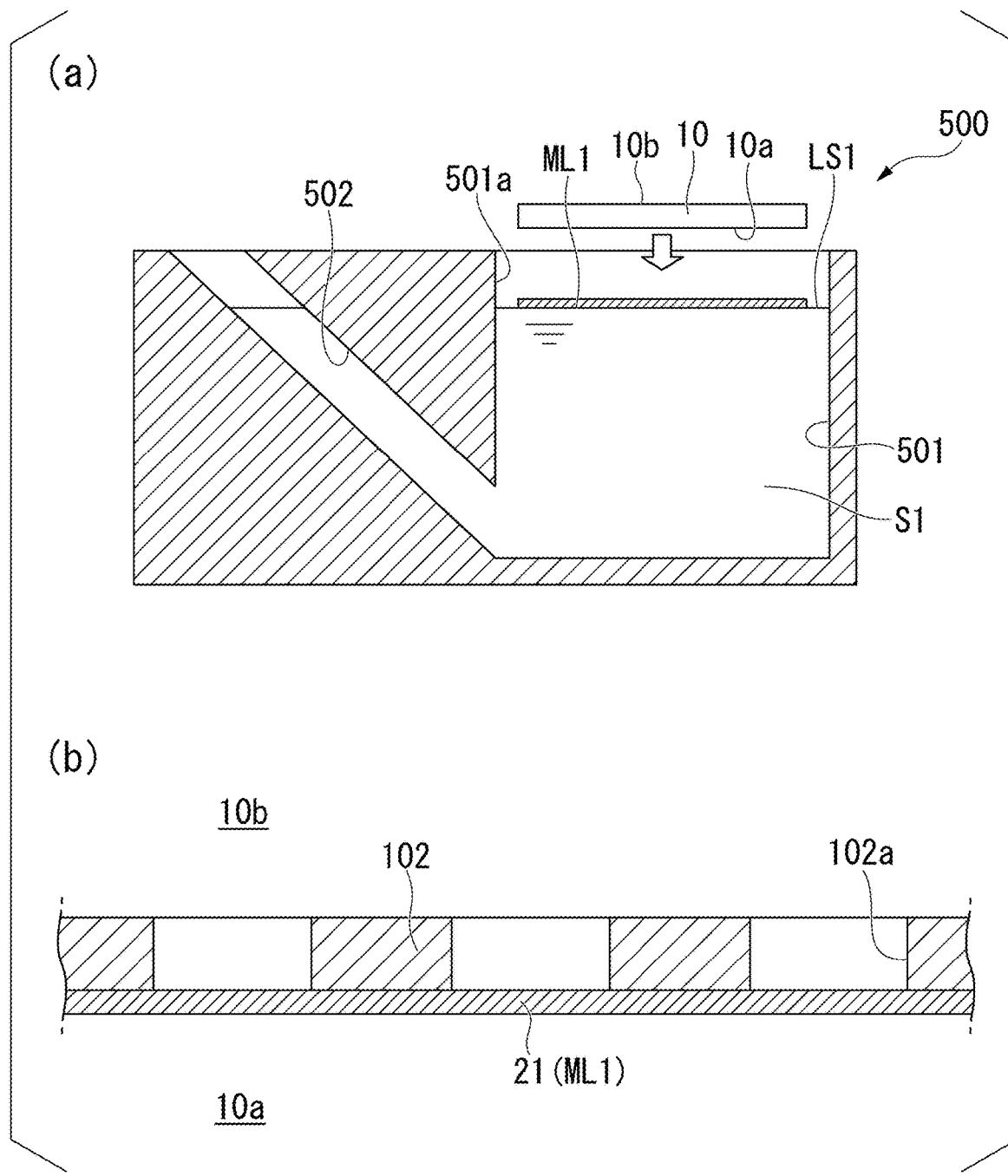
FIG. 6 is an illustrative diagram showing the method of producing a membrane protein analysis substrate according to the first embodiment.

FIG. 1 is a schematic perspective view of the membrane protein analysis substrate 1 and the membrane protein analysis grid 90, FIG. 2 is an arrow cross-sectional view taken along the line II-II in FIG. 1, FIG. 3 is a partially enlarged view of the membrane protein analysis substrate 1 and the membrane protein analysis grid 90, and FIG. 4 is an arrow cross-sectional view taken along the line IV-IV in FIG. 3.

In the following description, the membrane protein analysis substrate will be referred to as an "analysis substrate."

As shown in FIGS. 1 to 4, an analysis substrate 1 includes an electron microscope grid 10, a lipid bilayer membrane 20, and membrane proteins 30.

In addition, the membrane protein analysis grid 90 includes the electron microscope grid 10 and the lipid bilayer membrane 20. Hereinafter, the "electron microscope grid" will be simply referred to, as a "grid."

<Grid>

The grid 10 includes a grid body 101 and a microgrid membrane 102. The grid 10 corresponds to the "electron microscope grid" in the present invention.

The grid, body 101 is formed of a metal material, and a plurality of body through-holes 101a that penetrate in the thickness direction (penetrate from a first surface 10a of the grid 10 toward a second surface 10b). The grid body 101 according to the present embodiment has a plurality of body through-holes 101a that are rectangular in a plan view and arranged in a matrix.

Here, the shape of the body through-hole 101a in a plan view in the drawing is an example, and various shapes used in known grids can be used as the shape of the body through-hole 101a. In addition, the number of body through-holes 101a shown in the drawing is an example, and can be changed. In the drawing, a plurality of body through-holes 101a are shown, but one body through-hole 101a may be used.

As shown in FIG. 2, the microgrid membrane 102 is provided on one surface (on the side of the second surface 10b of the grid 10) of the grid body 101. The microgrid membrane 102 is exposed to the inside of the body through-hole 101a.

The surface of the microgrid membrane 102 is hydrophobic. When the surface of the microgrid membrane 102 is hydrophobic, a lipid monolayer constituting a lipid bilayer membrane to be described below easily adheres to the surface of the microgrid membrane 102.

As shown in FIG. 3, the microgrid membrane 102 has a plurality of through-holes 102a that are circular in a plan view and arranged in a matrix. The through-hole 102a of the microgrid membrane 102 corresponds to a "through-hole" in the present invention. The through-hole 102a is exposed to the inside of the body through-hole 101a in a plan view.

Here, the shape of the through-hole 102a in a plan view is not limited to a circular shape, and may be an elliptical shape, a rectangular shape, or a square shape.

The diameter of the through-hole 102a may be, for example, 0.4 μm or more and 4.0 μm or less. Here, the range of the diameter of the through-hole 102a is an example, and the present invention is not limited thereto.

Here, in the present embodiment, various materials can be used as long as the material of the microgrid membrane 102 is hydrophobic. The microgrid membrane 102 can be formed of a plastic membrane or carbon membrane as a material. As the material of the plastic membrane, for example triafol (cellulose acetate butyrate), formvar or collodion can be used.

In addition, the hydrophobic microgrid membrane 102 may be a laminated membrane of a plastic membrane and a carbon membrane. The surface of the carbon 25 membrane may be covered with the above plastic membrane as a material.

In observation under a general electron microscope, in order to adsorb a hydrophilic sample to a grid, the grid is subjected to a glow discharge treatment to make the surface of the grid hydrophilic. However, in the grid 10 used in the present embodiment, in order to make the microgrid membrane 102 hydrophobic, the hydrophilization treatment is not performed.

<Lipid Bilayer Membrane>

As shown in FIG. 4, the lipid bilayer membrane 20 is provided to cover at least one of the plurality of through-holes 102a. The lipid bilayer membrane 20 may cover the through-hole 102a so that the through-hole 102a is completely blocked, or may cover a part of the through-hole 102a.

The lipid bilayer membrane of the membrane protein analysis substrate and the membrane protein analysis grid according to the present invention is a planar membrane, unlike general liposomes.

One lipid monolayer (a first lipid monolayer 21) constituting the lipid bilayer membrane 20 is larger than the through-hole 102a in a plan view and covers the first surface 10a of the grid 10. In addition, the other lipid monolayer (a second lipid monolayer 22) constituting the lipid bilayer membrane 20 is larger than the through-hole 102a in a plan view, and covers the second surface 10b of the grid 10.

The first lipid monolayer 21 positioned on the side of the first surface 10a and the second lipid monolayer 22 positioned on the side of the second surface 10b are bonded by matching respective hydrophobic groups inside each other inside the through-hole 102a to form the lipid bilayer membrane 20. A part in which the first lipid monolayer 21 and the second lipid monolayer 22 are bonded inside the through-hole 102a corresponds to the lipid bilayer membrane 20.

The first lipid monolayer 21 is formed of a plurality of first lipid molecules. In the first lipid monolayer 21, hydrophilic groups of the first lipid are arranged on the side opposite to the microgrid membrane 102, and hydrophobic groups of the first lipid are arranged on the side of the microgrid membrane 102.

The second lipid monolayer 22 is formed of a plurality of second lipid molecules. In the second lipid monolayer 22, hydrophilic groups of the second lipid are arranged on the side opposite to the microgrid membrane 102, and hydrophobic groups of the second lipid are arranged on the side of the microgrid membrane 102.

In the lipid bilayer membrane 20, the hydrophobic groups of the first lipid monolayer 21 and the hydrophobic groups of the second lipid monolayer 22 face each other.

The first lipid and the second lipid each may be a single molecule or a mixture of two or more lipid molecules.

In addition, the first lipid and the second lipid may be different lipids or may be the same lipid.

As the first lipid and the second lipid, either or both of a synthetic lipid and a natural lipid can be used. As the first lipid and the second lipid, known phospholipids constituting biological membranes and lipids used as models of biological membranes can be suitably used, and examples thereof include phosphatidyl choline such as PO phosphatidylcholine, phosphatidylethanolamine, and phosphatidylserine.

These lipids may be used alone or two or more thereof may be used in combination. For example, when a membrane that resembles a composition of a membrane on the side of a cytoplasm among human cell membranes is prepared, a mixture of phosphatidyl choline, phosphatidylethanolamine, and phosphatidylserine at a ratio of 1:1:3 may be used. In addition, cholesterol and phosphatidylinositol diphosphate may be added.

[Membrane Protein]

The membrane proteins 30 are retained in the lipid bilayer membrane 20. The membrane proteins 30 are objects to be analyzed according to a method of analyzing membrane proteins to be described below. The membrane proteins 30 are retained in the lipid bilayer membrane 20 formed at a position planarly overlapping the through-hole 102a. In addition, the membrane proteins 30 shown in the drawing are transmembrane proteins. The membrane protein that is an object to be analyzed is not limited to a transmembrane protein, and may be an integral membrane protein of which a part is embedded in the lipid bilayer membrane 20 or a peripheral membrane protein.

The membrane proteins 30 may be present alone in the lipid bilayer membrane 20 or may be an aggregate.

Examples of membrane proteins 30 include known membrane proteins such as G protein-coupled receptors, ion channels, transporters, membrane enzymes such as oligosaccharyltransferase, and tyrosine kinase receptors. In addition, examples of membrane proteins 30 include complexes of these membrane proteins and soluble proteins that bind to membrane proteins, and complexes of these membrane proteins and drugs.

In addition, the membrane proteins 30 also include artificial membrane proteins. Examples of artificial membrane proteins include proteins with a function of embedding in lipid bilayer membranes or a function of binding to lipid bilayer membranes. The function of embedding in a lipid bilayer membrane can be imparted, for example, by adding an artificial transmembrane helix to a soluble protein. The function of binding to a lipid bilayer membrane can be imparted, for example, by modifying a lipid to a soluble protein.

<<Method of Producing Membrane Protein Analysis Substrate>>

FIGS. 5 to 8 are illustrative diagrams showing a method of producing a membrane protein analysis substrate according to the present embodiment.

The method of producing a membrane protein analysis substrate according to the present embodiment includes a process of providing a first lipid monolayer on the first surface 10a of the grid 10 described above, a process of providing a second lipid monolayer on the second surface 10b of the grid 10 and forming a lipid bilayer membrane in which the first lipid monolayer and the second lipid monolayer are bonded, and a process of retaining membrane proteins in the lipid bilayer membrane.

(Process of Providing First Lipid Monolayer)

In the process of, providing a first lipid monolayer, the first lipid monolayer formed on a liquid surface of a first solution is brought into contact with the first surface 10a. In the present embodiment, first, using a container 500 shown in FIG. 5, a monolayer ML1 of a first lipid L1 is formed on a liquid surface LS1 of a first solution S1.

The container 500 has a storage part 501 that stores the first solution S1 and a side tube 502 that is connected to the lower side wall of the storage part 501 and communicates with the storage part 501. The storage part 501 has an opening 501a on the upper side. The diameter of the opening 501a and the inner diameter of the storage part 501 are larger than the diameter of the grid 10.

The first solution S1 is a buffer solution. As the first solution S1, for example, an aqueous solution containing Tris-HCl (50 mmol/L) (pH 8.0), NaCl (100 mmol/L), and $MgCl_2$ (10 mmol/L) can be used. Here, the values in parentheses indicate the concentration of each solute in the buffer solution.

Examples of other buffer solutions include the following aqueous solutions. In addition, known buffer solutions can be used as long as they are buffer solutions used in general biochemical experiments.

$Na_2PO_4$ (25 mmol/L), NaCl (150 mmol/L)

Tris-HCl (50 mmol/L) (pH 8.0), NaCl (100 mmol/L), imidazole (400 mmol/L)

Tris-HCl (20 mmol/L) (pH 7.5), NaCl 150 mmol/L), $MgCl_2$ (1 mmol/L), $MnCl_2$ (1 mmol/L)

For example, the first lipid L1 that is dissolved in a mixed solvent MS of chloroform:methanol=9:1 (volume ratio) at a concentration of 0.1 mg/ml, is used. When the obtained solution of the first lipid L1 is added dropwise to the liquid surface LS1 of the first solution S1 in the storage part 501, the membrane of the solution of the first lipid L1 is formed on the liquid surface. Then, the mixed solvent MS (chloroform and methanol) evaporates, and thus the monolayer ML1 of the first lipid L1 is formed on the liquid surface LS1 of the first solution S1.

Next, as shown in FIG. 6(a), when the first surface 10a of the grid 10 is made to face the liquid surface LS1 of the first solution S1, the grid 10 is placed on the liquid surface LS1. The grid 10 floats on the liquid surface LS1, and the monolayer ML1 of the first lipid L1 comes into contact with the first surface 10a.

The surface of the grid 10 used (the surface of the microgrid membrane 102) is hydrophobic.

Thereby, the monolayer ML1 is transferred to the first surface 10a of the grid 10 to form the first lipid monolayer 21. As shown in FIG. 6(b), the first lipid monolayer 21 covers the plurality of through-holes 102a of the microgrid membrane 102 from the side of the first surface 10a.

After the first lipid monolayer 21 is formed, when the first solution S1 is added from the side tube 502, the grid 10 also rises as the liquid surface LS1 rises. After the first solution S1 is added until the grid 10 is lifted above the upper end of the storage part 501, the grid 10 is removed.

(Process of Providing Second Lipid Monolayer)

Next, in the process of providing a second lipid monolayer, the second surface 10b is brought into contact with the second lipid monolayer formed on a liquid surface of a second solution. In the present embodiment, the second solution is stored in the container 500 having the same shape as that used in the process of providing a first lipid monolayer, and in the same method as in the process of providing a first lipid monolayer, the second lipid monolayer is formed on the liquid surface of the second solution.

Next, in the same method as in the process of providing a first lipid monolayer, when the second surface 10b of the grid 10 is made to face the liquid surface of the second solution, the grid 10 is placed on the liquid surface of the second solution. The grid 10 floats on the liquid surface of the second solution and the second lipid monolayer comes into contact with the second surface 10b.

Figure 7:
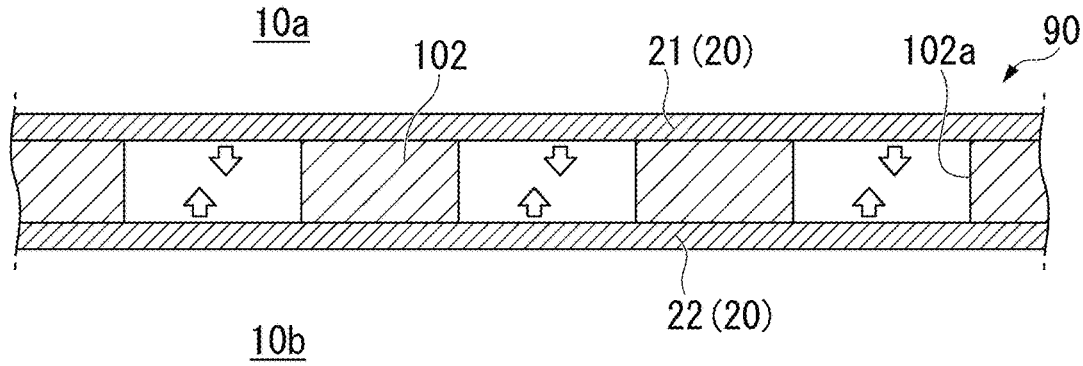
FIG. 7 is an illustrative diagram showing the method of producing a membrane protein analysis substrate according to the first embodiment.
Figure 8:
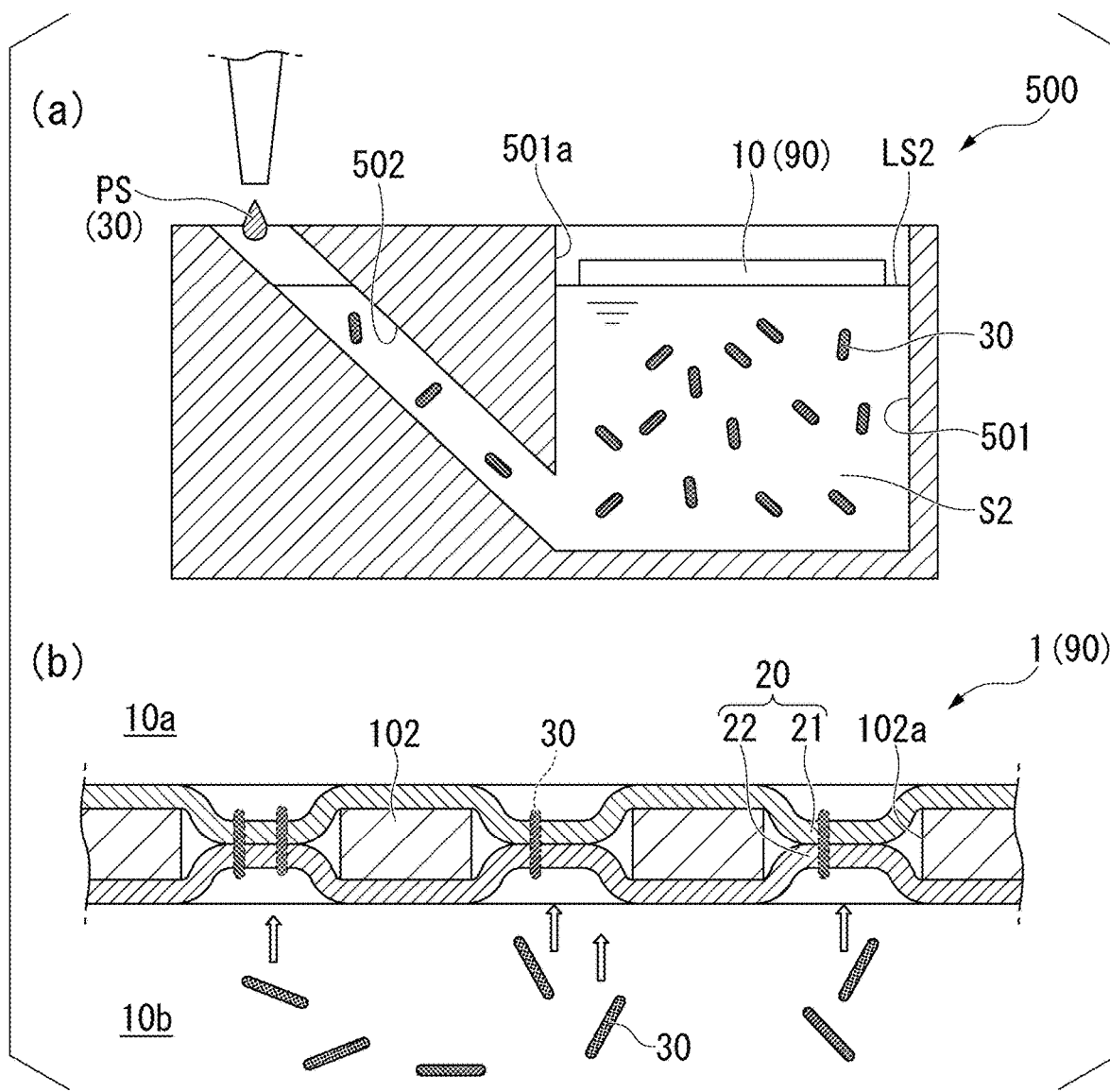
FIG. 8 is an illustrative diagram showing the method of producing a membrane protein analysis substrate according to the first embodiment.

Thereby, the second lipid monolayer is transferred to the second surface 10b of the grid 10, and the second lipid monolayer 22 is formed. As shown in FIG. 7, the second lipid monolayer 22 covers the plurality of through-holes 102a of the grid 10 from the side of the second surface 10b.

In addition, as shown in FIG. 7, the first lipid monolayer 21 and the second lipid monolayer 22 are attracted to each other inside the through-hole 102a and bonded according to a hydrophobic interaction, and the lipid bilayer membrane 20 is formed. Thereby, the membrane protein analysis grid 90 is obtained.

According to a combination of the first lipid and the second lipid used, the first lipid monolayer 21 and the second lipid monolayer 22 can form a "symmetric" lipid bilayer membrane having the same composition.

In addition, the first lipid monolayer 21 and the second lipid monolayer 22 can form an "asymmetric" lipid bilayer membrane having different compositions.

(Process of Retaining Membrane Proteins)

Next, in the process of retaining membrane proteins, as shown in FIG. 8(a), a solution PS containing membrane proteins is added from the side tube 502 to a second solution S2 stored in the storage part 501. The solution PS contains the membrane proteins 30 as objects to be analyzed. In the present embodiment, the membrane proteins 30 used as objects to be analyzed are solubilized in water (buffer solution). The solution PS is a buffer solution of solubilized membrane proteins 30. The membrane proteins 30 shown in the drawing are transmembrane proteins.

Examples of methods of solubilizing membrane proteins include a method using a surfactant, a method of embedding in liposomes, a method of embedding in a nanodisk that is a disk-shaped nanostructure, a method of embedding in a lipid bilayer membrane fragment prepared by a known method, and a method using an amphiphilic polymer (for example, amphipol). In addition, peripheral membrane proteins are soluble in many cases.

The membrane proteins 30 added to the second solution S2 diffuse into the second solution S2 and reaches the grid 10 (the membrane protein analysis grid 90) floating on a liquid surface LS2 of the second solution S2. As shown in FIG. 8(b), the membrane proteins 30 in the second solution S2 are inserted into the lipid bilayer membrane 20 formed on the grid 10 (the membrane protein analysis grid 90) and retained in the lipid bilayer membrane 20.

In the above method, when transmembrane proteins are used as the membrane proteins 30, other integral membrane proteins or peripheral membrane proteins may be used. When peripheral membrane proteins are used, the membrane proteins 30 bind to the surface of the lipid bilayer membrane 20.

Here, when the membrane proteins 30 contained in the solution PS are solubilized with a surfactant after the solution PS is added to the second solution S2, a surfactant adsorbent is additionally added to the second solution S2 from the side tube 502, and the surfactant may be removed from the second solution S2. Thereby, insertion of the membrane proteins 30 into the lipid bilayer membrane 20 is facilitated.

As the surfactant adsorbent, Bio-Beads SM-2 (commercially available from Bio-Rad Laboratories, Inc.) can be used.

In addition, when the solution PS is added to the second solution S2, the amount of the solution PS is limited to a small amount, and the concentration of the surfactant in the second solution S2 may be controlled to be low. Thereby, similar to the case, of using, the above surfactant adsorbent, insertion of the membrane proteins 30 into the lipid bilayer membrane 20 is facilitated.

Accordingly, it is possible to produce the membrane protein analysis substrate 1 in which the lipid bilayer membrane 20 retaining the membrane proteins 30 is formed in the through-holes 102a of the grid 10 (the membrane protein analysis grid 90).

In addition, in the above method, compared to when membrane proteins are embedded in lipid, bilayer membranes by other known methods, the membrane protein analysis substrate 1 can be suitably produced even if the amount of membrane proteins used is small.

When membrane proteins are embedded in lipid bilayer membranes by the above method, most of the lipid bilayer membranes present in the container 500 are retained in the grid 10 in a retrievable manner. Therefore, in the above method, when the membrane proteins 30 are retained in a limited amount of the lipid bilayer membrane 20, the membrane proteins 30 are concentrated in the lipid bilayer membrane 20 as a result. The concentrated membrane proteins 30 can be efficiently recovered by recovering the lipid bilayer membrane 20 together with the grid 10.

That is, in the above method, even if the amount of the membrane proteins 30 used is small, the membrane proteins 30 are efficiently concentrated in the lipid bilayer membrane 20, and additionally, the membrane proteins 30 retained in the lipid bilayer membrane 20 can be efficiently recovered. Therefore, in the above method, compared to other known methods, even if the amount of membrane proteins used is small, the membrane proteins 30 can be efficiently retained in the lipid bilayer membrane 20 to produce the membrane protein analysis substrate 1.

In addition, in the method of producing a membrane protein analysis substrate according to the present embodiment, for example, compared to a method using a nanodisk, a membrane protein analysis substrate can be produced in a shorter time, and within 12 hours when production is efficiently performed.

In addition, in the method of producing a membrane protein analysis substrate according to the present embodiment, for example, compared to a method using a nanodisk, a membrane protein analysis substrate can be produced more simply.

<<Method of Analyzing Membrane Protein>>

The method of analyzing membrane proteins according to the present embodiment includes a process of observing membrane proteins retained by the above analysis substrate or an analysis substrate produced by the above method of producing a membrane protein analysis substrate under an electron microscope. Since the membrane protein analysis substrate 1 includes the electron microscope grid 10, the grid 10 can be installed in an electron microscope and the membrane proteins can be observed.

Before the process of observing under an electron microscope, the membrane proteins 30 retained in the lipid bilayer membrane 20 may be stained. As the staining method, for example, known methods used for negative staining of protein samples and known immunostaining can be used.

In addition, in observation under an electron microscope, the membrane proteins 30 may be observed by a low-temperature electron microscope method. Generally, in the low-temperature electron microscope method, thin vitreous ice is prepared in the through-holes of the microgrid membrane, the sample in the ice is observed, but it is difficult to prepare thin ice retaining the sample without interferring with observation. On the other hand, in the method described in the present embodiment, since the sample is retained in the lipid membrane, there is an advantage of the sample with an appropriate thickness retained in the thin film (lipid bilayer membrane) being easily obtained by appropriately removing the solvent from the solution used during sample preparation. In addition, when membrane proteins are retained in the lipid bilayer membrane, the membrane proteins can be kept away from the gas-liquid interface of the solvent so that it can be expected that the membrane proteins will be less likely to denaturate.

When the membrane proteins 30 are observed by the low-temperature electron microscope method, the membrane proteins 30 may or may not be stained.

In addition, it is conceivable that, in a sample solution in which membrane proteins solubilized by a conventional method are dissolved, the membrane proteins receive an isotropic force in the solution and are not oriented. It is conceivable that, when observation is performed by the low-temperature electron microscope method using such a sample solution, the membrane proteins during observation are not oriented, and it is difficult to determine the orientation of the membrane proteins during analysis.

On the other hand, in the method described in the present embodiment, there is an advantage of facilitating determination of the orientation of the membrane proteins during analysis because the orientation of the membrane proteins in the vertical direction with respect to the lipid bilayer membrane is aligned to some extent.

From the obtained electron microscope image, membrane protein structure information is obtained by known analysis methods such as an electron beam tomographic method, a single particle analysis method, a structure analysis method using two-dimensional crystals, and a subtomogram averaging method.

According to the membrane protein analysis substrate having the configuration described above, membrane proteins can be easily analyzed in the analysis substrate. In addition, it is possible to provide a method of producing a membrane protein analysis substrate which allows membrane proteins retained in a lipid bilayer membrane to be easily formed in an electron microscope grid. In addition, it is possible to provide a method of analyzing membrane proteins using a membrane protein analysis substrate. In addition, it is possible to provide a membrane protein analysis grid having a lipid bilayer membrane.

Here, in the present embodiment, when the grid 10 is brought into contact with the monolayer ML1 formed on the liquid surface of the first solution S1, the monolayer ML1 is transferred to the first surface 10a of the grid 10, but the present invention is not limited thereto. If a lipid monolayer can be provided on the first surface 10a of the grid 10, the first lipid monolayer 21 may be formed by other known methods.

Similarly, if a lipid monolayer can be provided on the second surface 10b of the grid 10, the second lipid monolayer 22 may be formed by other known methods.

The method of forming the lipid bilayer membrane 20 is not limited to the methods described above, and known methods such as a painting method, a Montal-Mueller method, and a vesicle fusion method may be used.

In addition, in the present embodiment, the membrane proteins 30 are inserted into the lipid bilayer membrane 20 using the container 500 having the side tube 502, but the present invention is not limited thereto. For example, a buffer solution containing the membrane proteins 30 is put into a container different from the container 500, a surfactant adsorbent is put into the container, and the grid 10 having the lipid bilayer membrane 20 prepared separately is then made to float on the liquid surface of the buffer solution and thus the membrane proteins 30 may be inserted into the lipid bilayer membrane 20.

Second Embodiment

Figure 9:
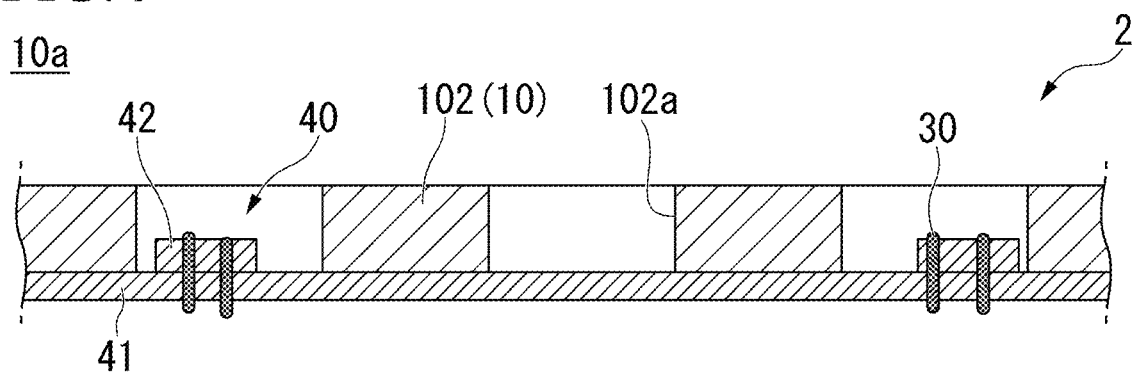
FIG. 9 is a schematic cross-sectional view of a membrane protein analysis substrate 2 according to a second embodiment.
Figure 10:
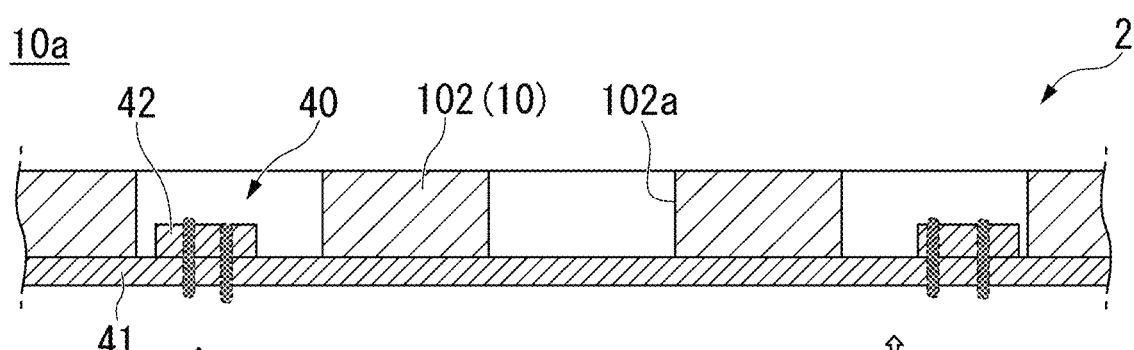
FIG. 10 is an illustrative diagram showing a method of producing a membrane protein analysis substrate according to the second embodiment.

FIGS. 9 and 10 are illustrative diagrams showing a membrane protein analysis substrate 2 and a method of producing a membrane protein analysis substrate according to a second embodiment. In the present embodiment, components the same as those in the first embodiment are denoted with the same reference numerals, and detailed descriptions will be omitted.

FIG. 9 is a schematic cross-sectional view of the membrane protein analysis substrate 2, and is a view corresponding to FIG. 4. As shown in FIG. 9 the analysis substrate 2 includes the grid 10, a lipid bilayer membrane 40, and the membrane proteins 30.

The lipid bilayer membranes 40 are discretely provided inside the through-hole 102a, and two lipid monolayers 41 and 42 constituting the lipid bilayer membrane 40 are formed of a same lipid.

The lipid monolayer 41 is larger than the through-hole 102a in a plan view, and covers one surface of the grid 10 from the side of the second surface 10b of the grid 10, and adheres to the grid 10. The lipid monolayer 41 covers the plurality of through-holes 102a from the side of the second surface 10b. Here, as long as the lipid monolayer 41 covers the through-hole 102a from the side of the second surface 10b, the position overlapping the through-hole 102a in a plan view may be partially broken.

The lipid monolayers 42 are discretely provided inside the plurality of through-holes 102a. The lipid monolayer 42 covers a part of the through-hole 102a inside the through-hole 102a and overlaps the lipid monolayer 41. A part of the lipid monolayer 41 and the lipid monolayer 42 are bonded inside the through-hole 102a to form the lipid bilayer membrane 40, and cover the through-hole 102a.

The membrane proteins 30 are retained in the lipid bilayer membrane 40.

<<Method of Producing Membrane Protein Analysis Substrate>>

FIG. 10 is an illustrative diagram showing a method of producing a membrane protein analysis substrate. The method of producing a membrane protein analysis substrate according to the present embodiment includes a process of bringing one surface of an electron microscope grid into contact with a lipid monolayer formed on a liquid surface of a solution and forming a lipid bilayer membrane inside a plurality of through-holes and a process of adding membrane proteins to the solution to retain the membrane proteins in the lipid bilayer membrane.

The same solution as the first solution S1 in the first embodiment can be used as a solution for forming a lipid monolayer. Hereinafter, a solution for forming a lipid monolayer in the present embodiment will be referred to as a solution S3.

For the lipid, the same lipid as the first lipid in the first embodiment can be used.

First, the solution S3 is stored in the container 500 having the same shape as that used in the first embodiment, and a lipid monolayer is formed on the liquid surface of the solution S3 by the same method as the process of providing a first lipid monolayer according to the first embodiment.

Next, in the same method as in the process of providing a first lipid monolayer according to the first embodiment, when one surface of the grid 10 (the second surface 10*b*) is made to face the liquid surface of the solution, the grid 10 is placed on the liquid surface of the solution S3. The grid 10 floats on the liquid surface of the solution S3, and the lipid monolayer comes into contact with the second surface 10*b*.

The surface of the grid 10 used (the surface of the microgrid membrane 102) is hydrophobic.

Thereby, the lipid monolayer is transferred to the second surface 10*b* of the grid 10. As shown in FIG. 10, the lipid monolayer 41 covers the through-holes 102*a* of the microgrid membrane 102 from the side of the second surface 10*b*.

Thereby, as shown in FIG. 10, the lipid monolayer 41 is formed on the second surface 10*b* of the grid 10. The lipid monolayer 41 covers the through-holes 102*a* of the grid 10 from the side of the second surface 10*b*.

In addition, a part of the lipid monolayer 41 forms a self-assembled lipid bilayer membrane 40 inside the plurality of through-holes 102*a*. The formed lipid bilayer membrane 40 is a "symmetric" lipid bilayer membrane in which the lipid monolayer 41 and the lipid monolayer 42 formed from a part of the lipid monolayer 41 are bonded.

The lipid monolayer 42 is not guaranteed to be formed in all through-holes 102*a*, and is generally discretely formed inside a plurality of through-holes 102*a*. In addition, the lipid monolayer 42 does not completely block the through-hole 102*a* in a plan view and covers a part of the through-hole 102*a*.

In addition, as in the process of retaining membrane proteins according to the first embodiment, a solution containing membrane proteins is added to the solution S3 of the storage part 501 from the side tube 502 of the container 500. As shown in FIG. 10, the membrane proteins 30 in the solution S3 are inserted into the lipid bilayer membrane 40 from the solution S3 and retained in the lipid bilayer membrane 40. In the solution containing membrane proteins, the membrane proteins are solubilized with a surfactant or the like.

When a solution containing membrane proteins is added to the solution S3, the amount of the solution containing membrane proteins may be limited, and the concentration of the surfactant in the solution S3 may be controlled to be low. Thereby, insertion of the membrane proteins 30 into the lipid bilayer membrane 40 is facilitated.

In addition, when a solution containing membrane proteins is added to the solution S3, a surfactant adsorbent may be additionally added to the solution S3 from the side tube 502, and the surfactant may be removed from the solution S3. Thereby, insertion of the membrane proteins 30 into the lipid bilayer membrane 40 is facilitated.

Accordingly, the membrane protein analysis substrate in which the lipid bilayer membrane 40 retaining the membrane proteins 30 is formed in the through-hole 102*a* of the grid 10 can be produced.

Like the membrane protein analysis substrate 1, the obtained membrane protein analysis substrate 2 can be used for analysis of membrane proteins using an electron microscope.

The membrane protein analysis substrate having the configuration described above also serves as an analysis substrate which allows membrane proteins to be easily analyzed. In addition, it is possible to provide a method of producing a membrane protein analysis substrate which allows membrane proteins retained in a lipid bilayer membrane to be easily formed in an electron microscope grid. In addition, it is possible to provide a method of analyzing membrane proteins using a membrane protein analysis substrate.

Third Embodiment

Figure 11:
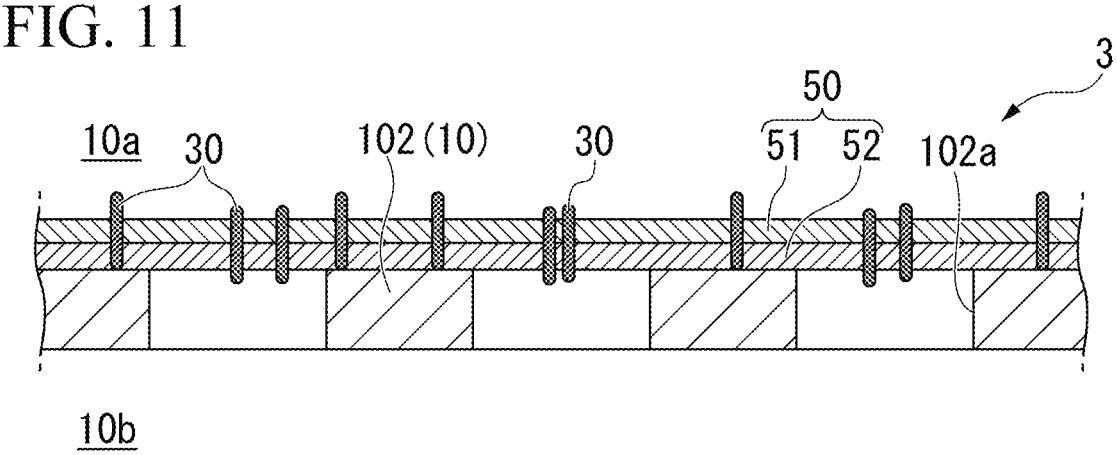
FIG. 11 is a schematic cross-sectional view of a membrane protein analysis substrate 3 according to a third embodiment.

FIG. 11 is an illustrative diagram of a membrane protein analysis substrate 3 according to a third embodiment. In the present embodiment, components the same as those in the first and second embodiments are denoted with the same reference numerals, and detailed descriptions will be omitted.

FIG. 11 is a schematic cross-sectional view of the membrane protein analysis substrate 3, and is a view corresponding to FIG. 4. As shown in FIG. 11 the analysis substrate 3 includes the grid 10, a lipid bilayer membrane 50, and the membrane proteins 30.

The lipid bilayer membrane 50 covers the plurality of through-holes 102*a* from one surface of the grid 10 (the first surface 10*a*). The lipid bilayer membrane 50 is provided at a position planarly overlapping the microgrid membrane 102 in addition to the position planarly overlapping the through-hole 102*a*.

Two lipid monolayers 51 and 52 constituting the lipid bilayer membrane 50 may be formed of different lipids or may be formed of the same lipid. The lipid monolayers 51 and 52 are larger than the through-hole 102*a* in a plan view.

The membrane proteins 30 are retained in the lipid bilayer membrane 50. The membrane proteins 30 are arranged on the entire surface of the lipid bilayer membrane 50, and are arranged at the position planarly overlapping the microgrid membrane 102 in addition to the position planarly overlapping the through-hole 102*a*.

<<Method of Producing Membrane Protein Analysis Substrate>>

The method of producing a membrane protein analysis substrate according to the present embodiment includes a process of forming, a lipid bilayer membrane retaining membrane proteins and a process of transferring the lipid bilayer membrane retaining the membrane proteins to one surface of an electron microscope grid having a plurality of through-holes. The lipid bilayer membrane used includes, as a component, a lipid monolayer larger than the through-hole 102a in a plan view.

That is, in the present embodiment, a lipid bilayer membrane retaining membrane proteins at a location different from that of the electron microscope grid is formed, and the obtained lipid bilayer membrane is moved to the grid to produce a membrane protein analysis substrate.

In the process of forming a lipid bilayer membrane retaining membrane proteins, the method of forming a lipid bilayer membrane may be known method, and the same method as in the "process of providing a first lipid monolayer" and "process of providing a second lipid monolayer" according to the first embodiment may be used. Examples of an object for forming a lipid bilayer membrane include a hydrophobic film having a through-hole.

The formed lipid bilayer membrane may be a "symmetric" lipid bilayer membrane or an "asymmetric" lipid bilayer membrane.

The method of retaining membrane proteins in a lipid bilayer membrane may be a known method or may be the same method as in the "process of retaining membrane proteins" according to the first embodiment. For example, when membrane proteins are solubilized with a surfactant, insertion of the membrane proteins into the lipid bilayer membrane can be facilitated by removing the surfactant, through dialysis.

For the process of transferring to one surface, for example, a method in which a circular wire is brought into contact with a lipid bilayer membrane retaining membrane proteins to transfer the lipid bilayer membrane to, the ring, and additionally, one surface of the grid is brought into contact with, the transferred lipid bilayer membrane to transfer the lipid bilayer membrane to the grid is an exemplary example.

Thereby, the lipid bilayer membrane transferred to one surface of the grid 10 covers the plurality of through-holes 102a of the grid 10 from one surface of the grid.

The surface of the grid 10 used (the surface of the microgrid membrane 102) is hydrophilic.

Accordingly, the membrane protein analysis substrate 3 can be produced.

Like the membrane protein analysis substrate 1, the obtained membrane protein analysis substrate 3 can be used for analysis of membrane proteins using an electron microscope.

The membrane protein analysis substrate having the configuration described above also serves as an analysis substrate which allows membrane proteins to be easily analyzed. In addition, it is possible to provide a method of producing a membrane protein analysis substrate which allows membrane proteins retained in a lipid bilayer membrane to be easily formed in an electron microscope grid. In addition, it is possible to provide a method of analyzing membrane proteins using a membrane protein analysis substrate.

While preferable exemplary embodiments according to the present inventions have been provided above with reference to the appended drawings, the present invention is not limited to such examples. Various shapes, combinations and the like of respective constituent members shown in the above examples are only examples, and can be variously changed based on product designs, product specifications and the like without departing from the spirit and scope of the present invention.

EXAMPLES

Hereinafter, the present invention will be described with reference to examples, but the present invention is not limited to these examples.

The following examples were performed under the following conditions.

Buffer Solution A

As a buffer solution A, an aqueous solution containing Tris-HCl (50 mmol/L) (pH 8.0), NaCl (100 mmol/L), and $MgCl_2$ (10 mmol/L) was used. The values in parentheses indicate the concentration of each solute in the buffer solution A.

Lipid

As a lipid for forming a lipid membrane, PO phosphatidylcholine (POPC, 1-palmitoyl-2-oleoyl-glycero-3-phosphocholine) was used. POPC was dissolved in a mixed solvent containing chloroform:methanol=9:1 (volume ratio) to prepare 0.1 mg/ml of a lipid solution.

Grid

A commercially available electron microscope grid (model number: Quantifoil R1.2/1.3 on 200 gold mesh, commercially available from Quantifoil Micro Tools) was used.

Container for Forming Lipid Bilayer Membrane

The container 500 used in the production method according to the first embodiment or the production method according to the second embodiment was used. The container 500 had the storage part 501 that stored the buffer solution A and the side tube 502 that was connected to the lower side wall of the storage part 501 and communicated with the storage part 501. The volume of the container 500 was 60 µl.

Formation of Lipid Bilayer Membrane

According to the production method according to the first embodiment or the production method according to the second embodiment, 1 µL of a lipid solution was added dropwise to the liquid surface of the buffer solution A stored in the storage part 501 of the container 500 and chloroform and methanol were then removed by evaporation and thus a lipid monolayer was formed on the liquid surface of the buffer solution A.

Using the formed lipid monolayer, according to the production method of the first embodiment or the production method of the second embodiment, a symmetric lipid bilayer membrane was formed on the surface of the grid.

Example 1

According to the production method of the first embodiment, membrane proteins were retained in the lipid bilayer membrane.

*E. coli* AcrB proteins were used as the membrane proteins. Specifically an aqueous solution (0.25 mg/ml) in which *E. coli* AcrB proteins were dissolved in the following buffer solution 1 was used. *E. coli* AcrB proteins were solubilized with a surfactant n-Dodecyl-β-D-maltoside (DDM) contained in the following buffer solution 1 and dissolved in the prepared buffer solution 1.

Buffer Solution 1

$Na_2PO_4$ (25 mmol/L), NaCl (150 mmol/L), DDM (0.2% (w/v))

Here, "% (w/w)" indicates mass volume %. The same applies to the description of the following specification.

1 µl of the *E. coli* AcrB protein suspension was added to 59 µl of the buffer solution A stored in the storage part 501 of the container 500 from the side tube 502, and membrane proteins were retained in the lipid bilayer membrane formed on the surface of the grid.

Example 2

According to the production method of the first embodiment, membrane proteins were retained in the lipid bilayer membrane.

AglB proteins of *Archaeoglobus fulgidus*, an archaeon, were used as the membrane protein. Specifically, an aqueous solution (0.35 mg/ml) in which archaeal AglB proteins were dissolved in the following buffer solution 2 was used. archaeal AglB proteins were solubilized with a surfactant DDM contained in the following buffer solution and dissolved in the prepared buffer solution 2.

Buffer Solution 2

Tris-HCl (50 mmol/L) (pH 8.0), NaCl (100 mmol/L), imidazole (400 mmol/L), DDM (0.1% (w/v))

3 µl of the archaeal AglB protein suspension was added to 57 µl of the buffer solution A stored in the storage part 501 of the container 500 from the side tube 502, and membrane proteins were retained in the lipid bilayer membrane, formed on the surface of the grid.

Example 3

According to the production method of the first embodiment, membrane proteins were retained in the lipid bilayer membrane.

Yeast OST complexes were used as the membrane proteins. Specifically, an aqueous solution (0.2 mg/ml) in which yeast OST complexes were dissolved in the following buffer solution 3 was used.

The yeast OST complexes were solubilized with a surfactant digitonin contained in the following aqueous solution and dissolved in the prepared buffer solution 3.

Buffer Solution 3

Tris-HCl (20 mmol/L) (pH 7.5), NaCl (150 mmol/L), $MgCl_2$ (1 mmol/L), $MnCl_2$ (1 mmol/L), digitonin (0.05% (w/v))

6 µl of the yeast OST complex aqueous solution was added to 54 µl of the buffer solution A stored in the storage part 501 of the container 500 from the side tube 502, and membrane proteins were retained in the lipid bilayer membrane formed on the surface of the grid.

Example 4

Membrane proteins were retained in, the lipid bilayer membrane in the same manner as in Example 1 except that membrane proteins were retained in the lipid bilayer membrane according to the production method of the second embodiment.

In Examples 1 to 4, according to a general method, the membrane proteins retained in the lipid bilayer membrane were negatively stained with uranyl acetate. After the negative staining, the grid was mounted on a sample stage of a transmission electron microscope (model number: FEI Tecnai T20, commercially available from FEI) to obtain an electron microscope image.

Figure 12:
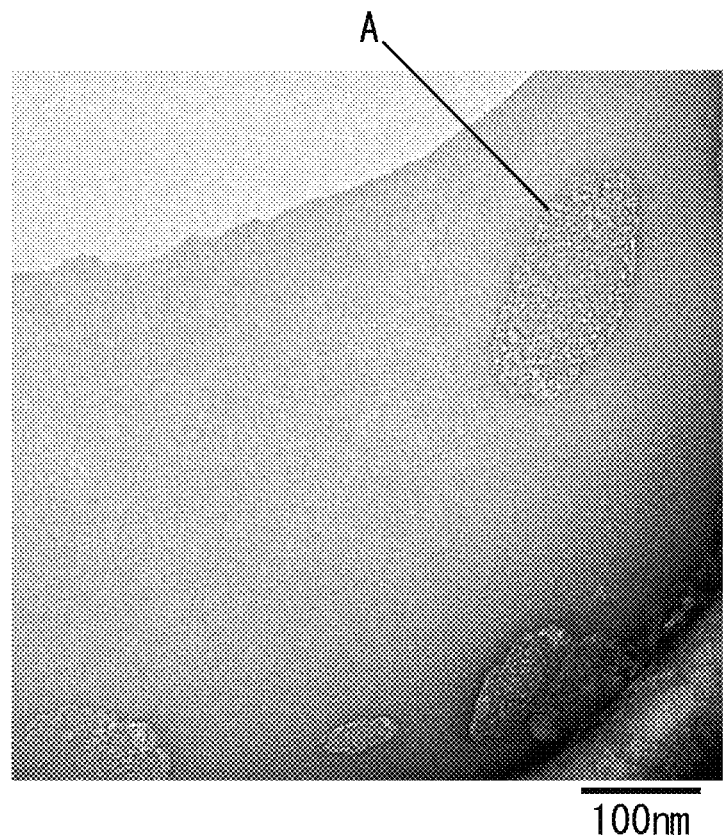
FIG. 12 is an electron microscope image of *E. coli* AcrB of Example 1.
Figure 13:
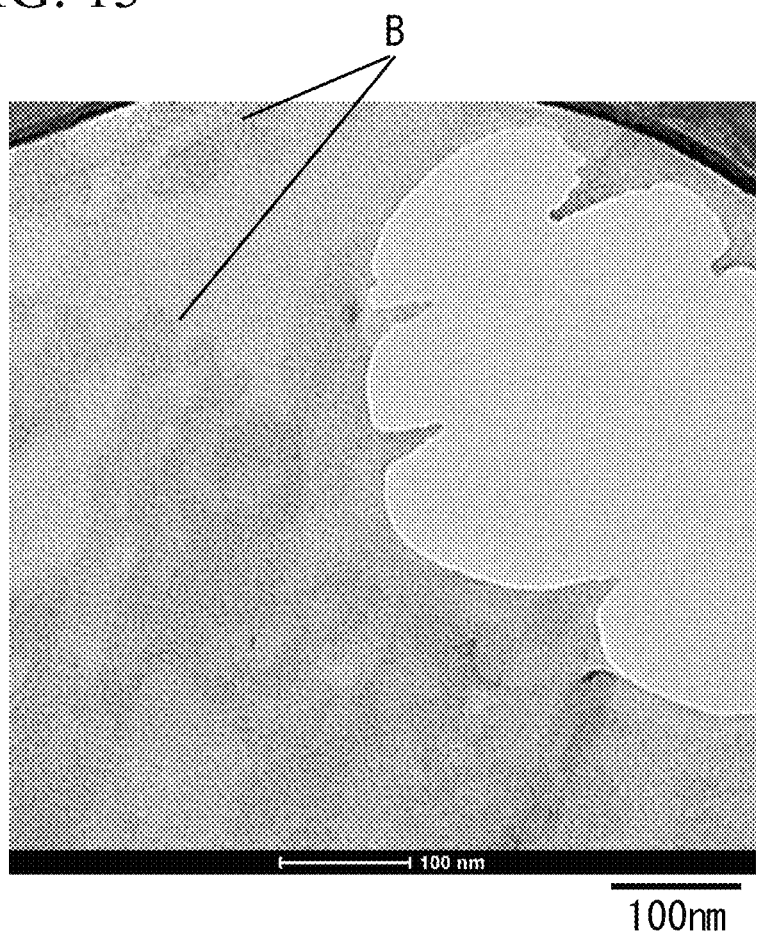
FIG. 13 is an electron microscope image of archaeal AglB of Example 2.
Figure 14:
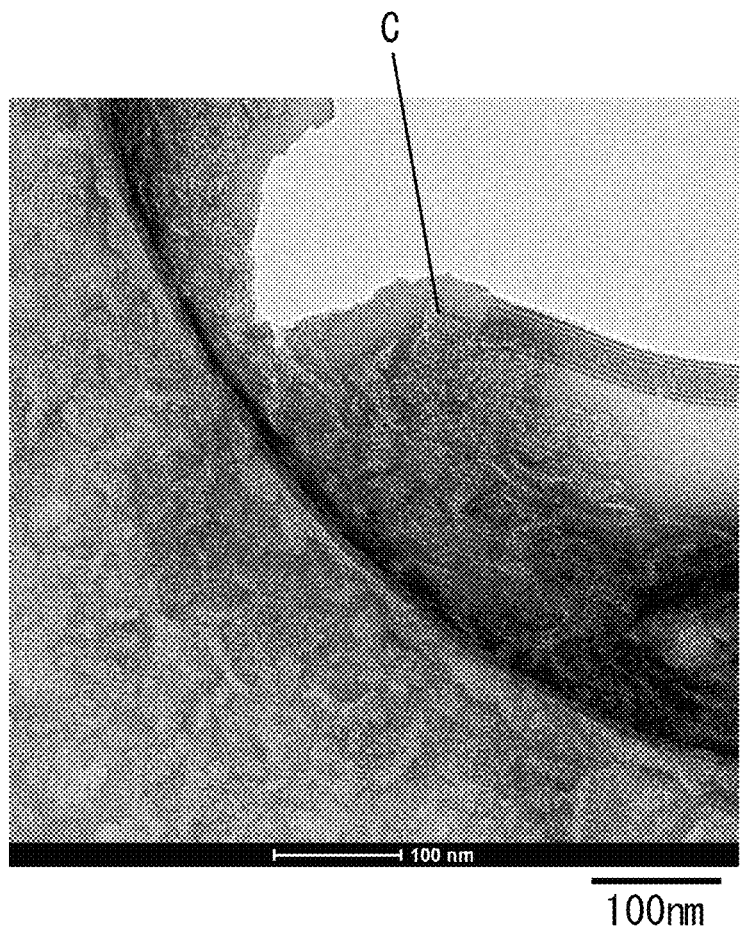
FIG. 14 is an electron microscope image of a yeast OST complex of Example 3.

FIGS. 12 to 14 are electron microscope images of the membrane proteins retained in the lipid bilayer membrane in Examples 1 to 3. In addition, in FIGS. 12 to 14, the analysis substrate was negatively stained and electron microscope images were captured.

FIG. 12 is an electron microscope image of *E. coli* AcrB of Example 1. It can be understood from FIG. 12 that *E. coli* AcrB formed an aggregate. In FIG. 12, the reference numeral A indicates an aggregate of *E. coli* AcrB.

FIG. 13 is an electron microscope image of archaeal AglB of Example 2. It can be understood from FIG. 13 that archaeal AglB formed an aggregate. In FIG. 13, the reference numeral B indicates an aggregate of archaeal AglB.

FIG. 14 is an electron microscope image of a yeast OST complex of Example 3. It can be understood from FIG. 14 that yeast OST complexes formed an aggregate, and some of them were dispersed. In FIG. 14, the reference numeral C indicates an aggregate of yeast OST complexes.

Figure 15:
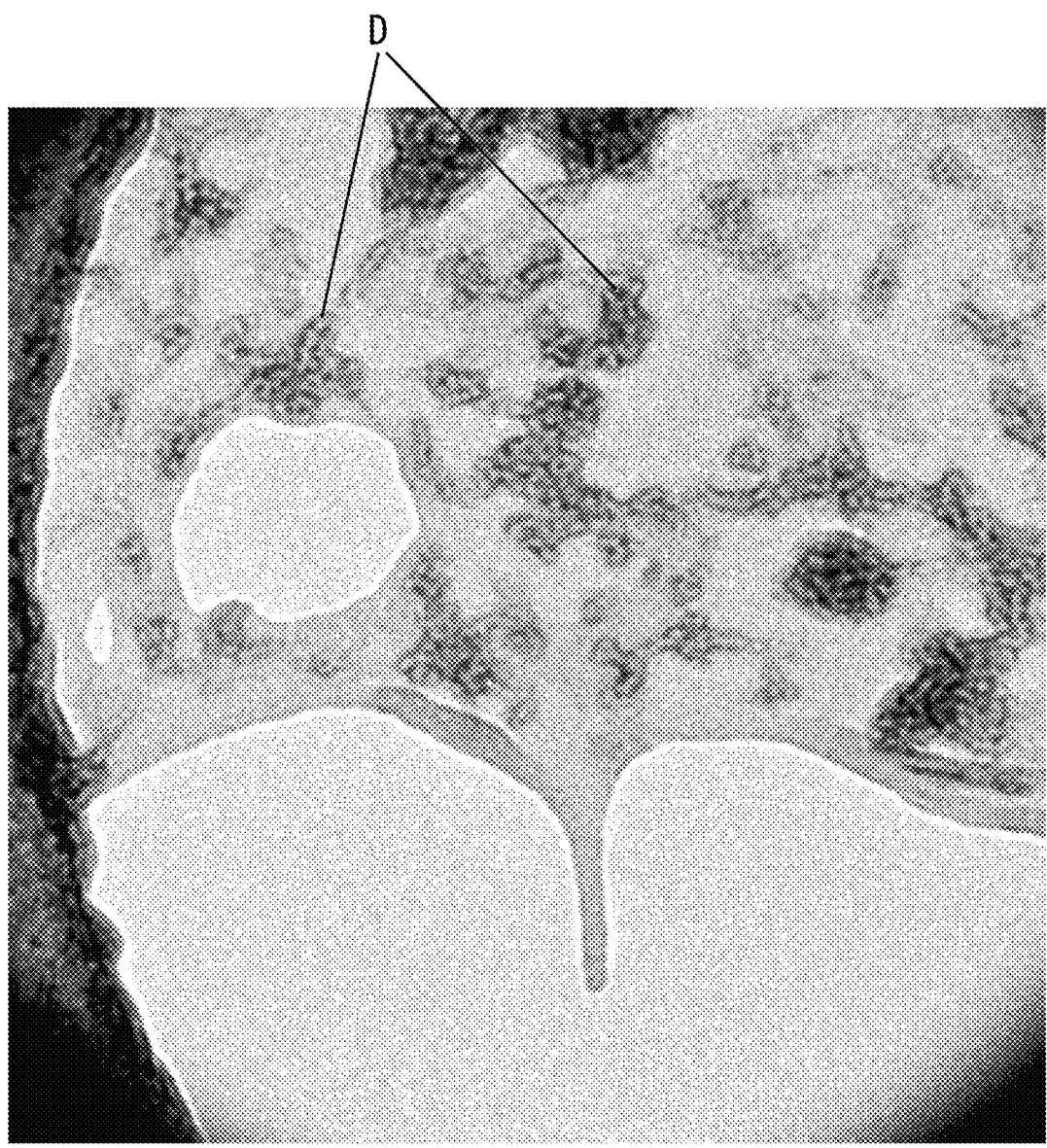
FIG. 15 is an electron microscope image of *E. coli* AcrB of Example 4.
Figure 16:
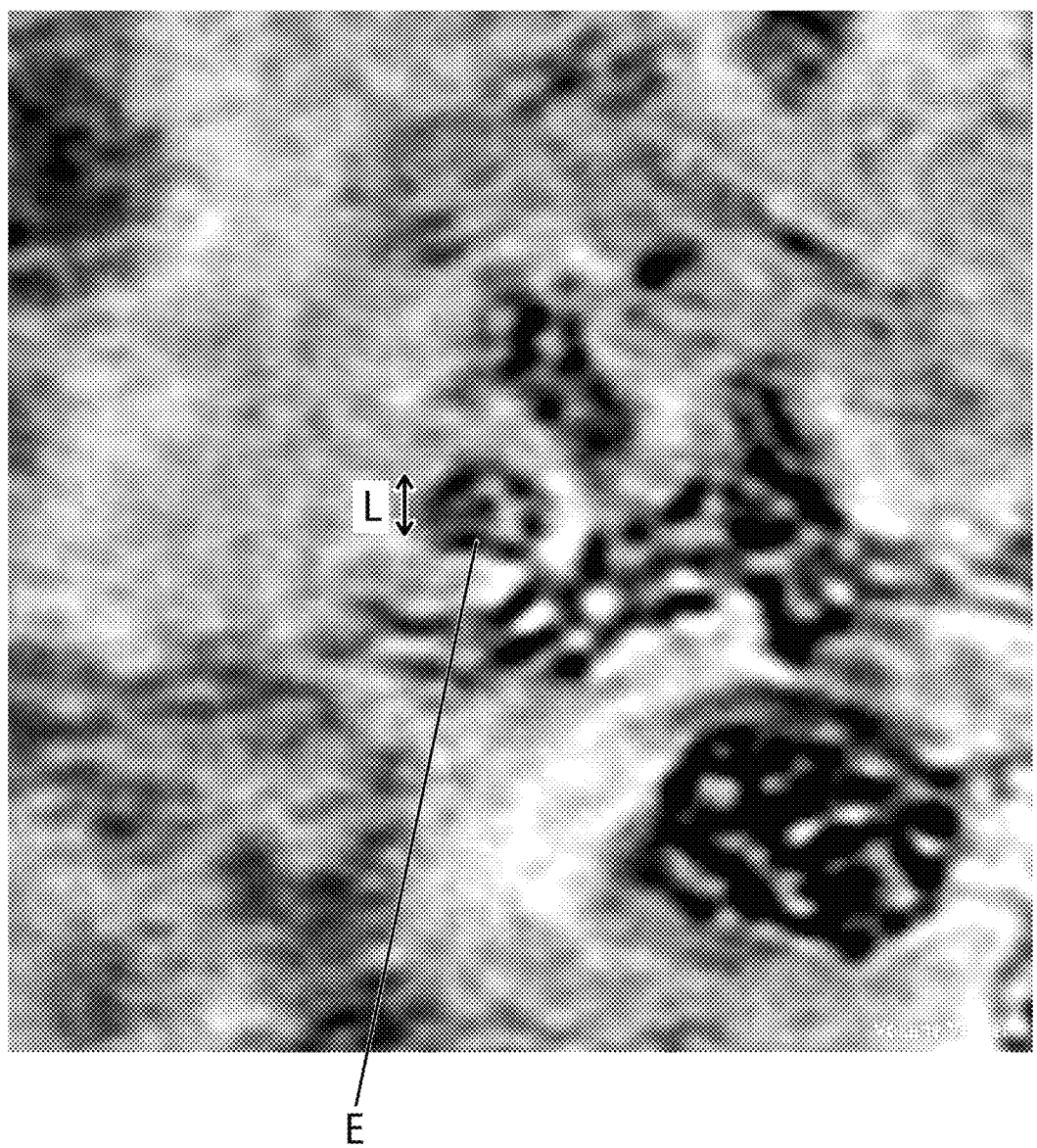
FIG. 16 is a cross-sectional image of a tomogram reconstructed from a series of tilted electron microscope images of *E. coli* AcrB of Example 4.

FIGS. 15 and 16 are electron microscope images of membrane proteins retained in the lipid bilayer membrane in Example 4.

FIG. 15 is an electron microscope image of *E. coli* AcrB. FIG. 15 is an electron microscope image after negative staining. It can be understood from FIG. 15 that *E. coli* AcrB formed an aggregate and some of them were dispersed. In FIG. 15, the reference numeral D indicates an aggregate of *E. coli* AcrB.

FIG. 16 is a cross-sectional image of a tomogram reconstructed from a series of tilted electron microscope images of *E. coli* AcrB. Specifically. FIG. 16 shows a cross section of a tomogram that was reconstructed from a series of tilted electron microscope images using image processing software (ImageJ: install plug-in program TomoJ).

FIG. 16 is drawn based on a tomogram reconstructed based on a series of electron microscope images obtained from negatively stained images of the same field of view as in FIG. 15. From FIG. 16, an image which is considered to be a trimer of *E. coli* AcrB could be confirmed.

In FIG. 16, the reference numeral E indicates a trimer of *E. coli* AcrB. In addition, in FIG. 16, the reference numeral L indicates a size of a trimer. In FIG. 16, the size L of the trimer was 11 nm.

Example 5

According to the production method of the second embodiment, membrane proteins were retained in the lipid bilayer membrane.

An aqueous solution in which *E. coli* AcrB proteins were dissolved in the buffer solution 1 was diluted with the buffer solution A to obtain an aqueous solution having an AcrB protein concentration of 0.025 mg/ml. 0.5 µl of the *E. coli* AcrB protein aqueous solution was added to 59.5 µl of the buffer solution A stored in the storage part 501 of the container 500 from the side tube 502, and membrane proteins were retained in the lipid bilayer membrane formed on the surface of the grid.

Example 6

According to the production method of the second embodiment, membrane proteins were retained in the lipid bilayer membrane.

Bacteriorhodopsin proteins from *Halobacterium salinarum*, archaebacterial, were used as the membrane proteins. Specifically, an aqueous solution (1 mg/ml) in which, bacteriorhodopsin proteins were suspended in the buffer solution A was used.

1 μl of the archaeal bacteriorhodopsin protein suspension was added to 59 μl of the buffer solution A stored in the storage part 501 of the container 500 from the side tube 502, and membrane proteins were retained in the lipid bilayer membrane formed on the surface of the grid.

Example 7

Archaeal AglB proteins were retained in the lipid bilayer membrane in the same manner as in Example 2 except that the membrane proteins were retained in the lipid bilayer membrane according to the production method of the second embodiment.

In Example 7, according to a general method, the membrane proteins retained in the lipid bilayer membrane were quickly frozen. After the quick freezing, the grid was mounted on a sample stage of a transmission electron microscope (model number: FEI Tecnai Polara, commercially available from FEI) to obtain an electron microscope image.

Example 8

Membrane proteins were retained in the lipid bilayer membrane in the same manner as in Example 4.

Then, the analysis substrate was immunostained using primary antibodies against a tag sequence attached to AcrB proteins and secondary antibodies against the primary antibodies (labeled with gold nanoparticles having a particle size of 6 nm).

FIGS. 17 to 20 are electron microscope images of the membrane proteins retained in the lipid bilayer membrane in Examples 5 to 8.

In Examples 5, 6, and 8, according to a general method, the membrane proteins retained in the lipid bilayer membrane were negatively stained with uranyl acetate. After the negative staining, the grid was mounted on a sample stage of a transmission electron microscope (model number: FEI Tecnai T20, commercially available from FEI) to obtain an electron microscope image.

Figure 17:
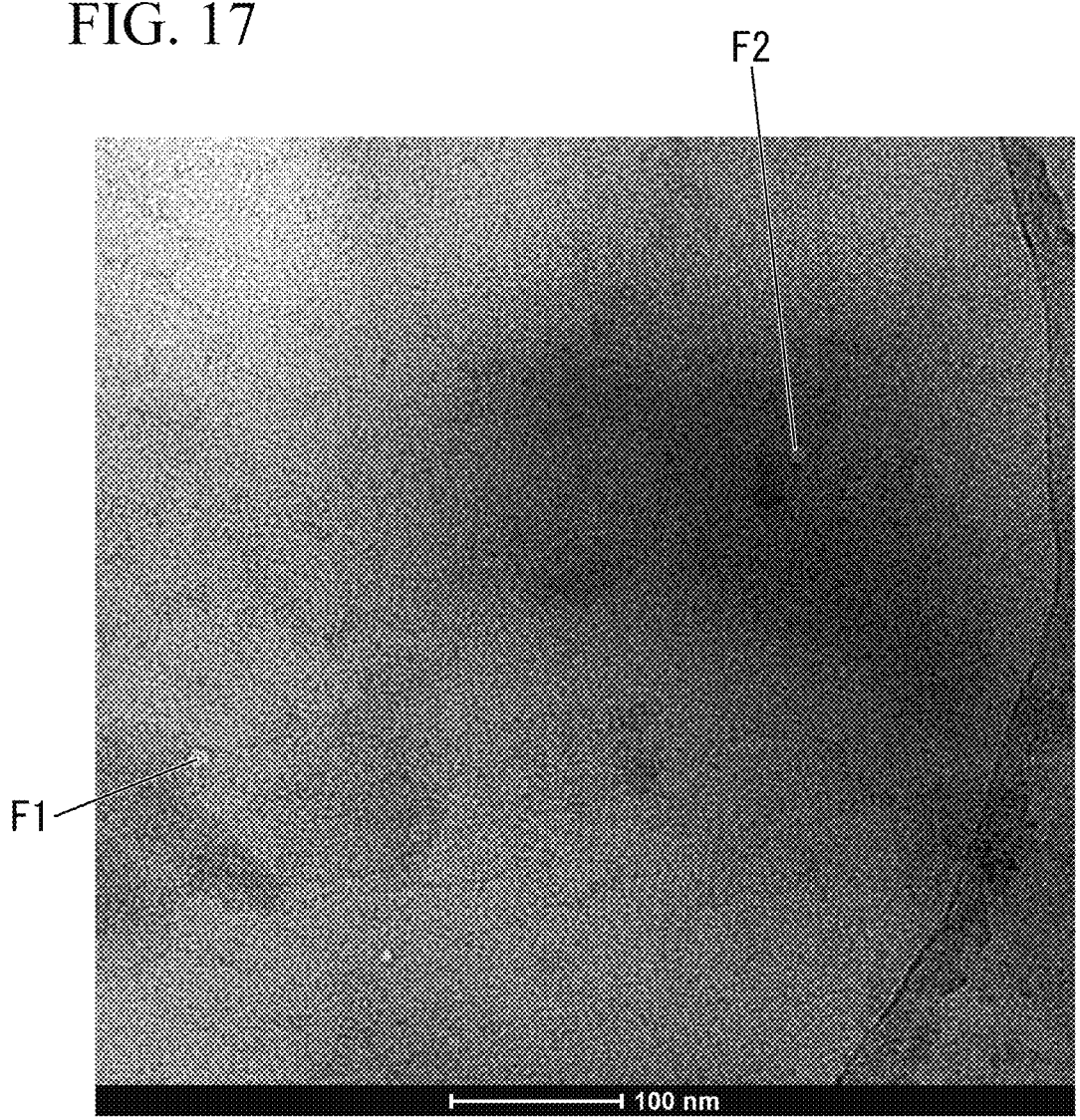
FIG. 17 is an electron microscope image of *E. coli* AcrB of Example 5.
Figure 18:
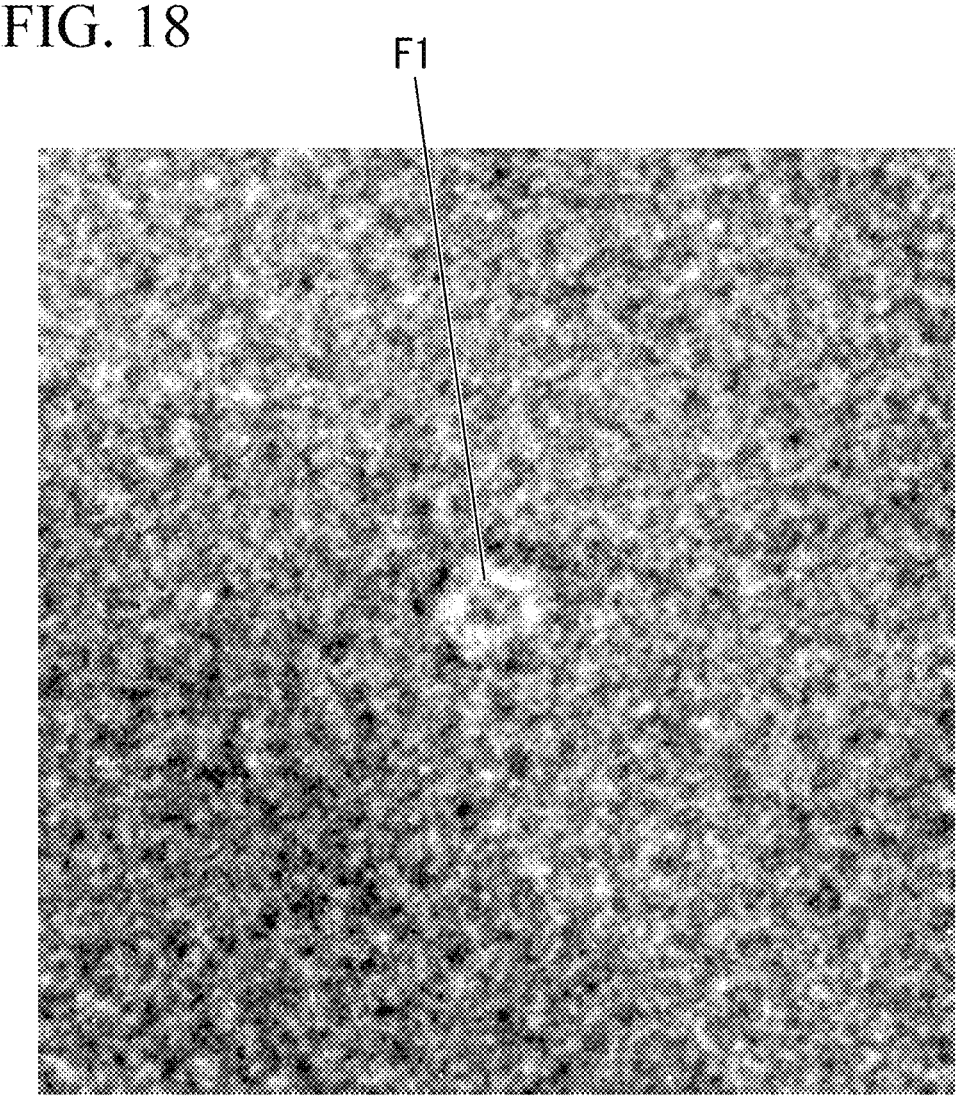
FIG. 18 is an electron microscope image of *E. coli* AcrB of Example 5.
Figure 19:
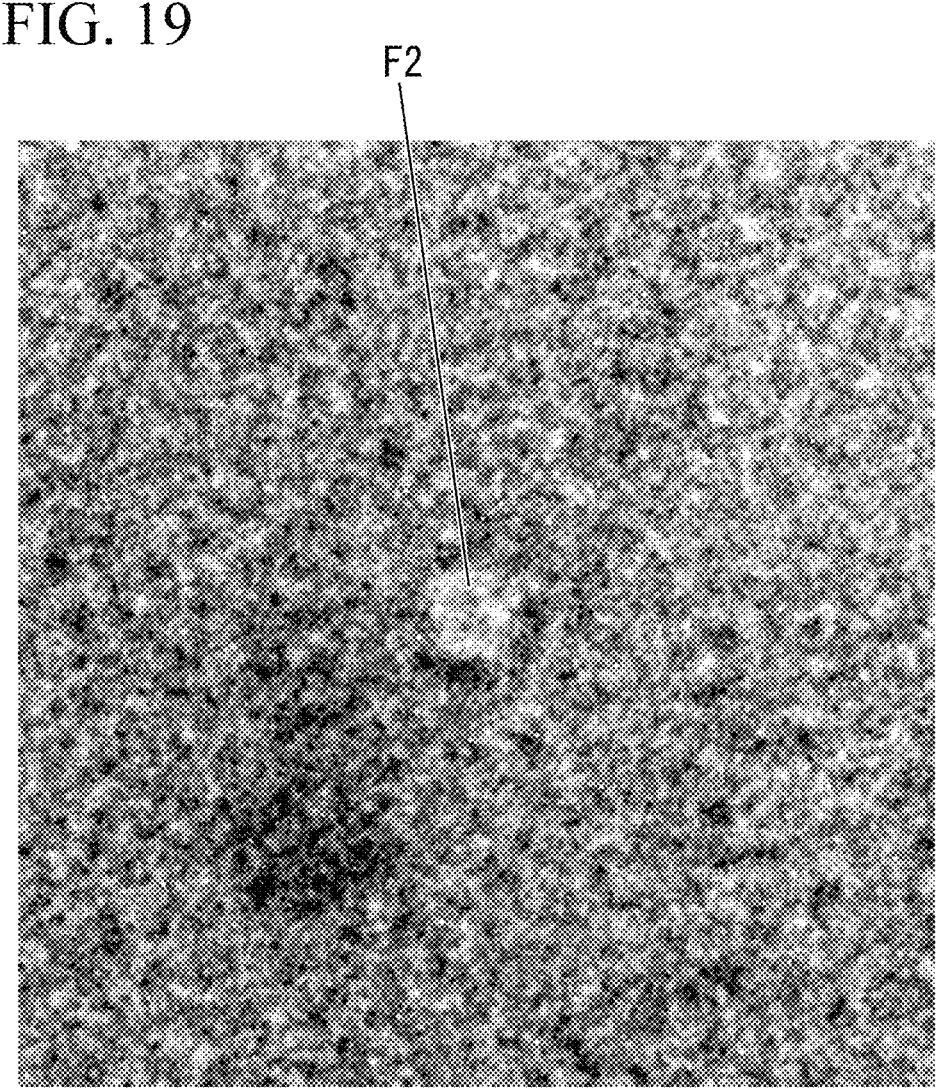
FIG. 19 is an electron microscope image of *E. coli* AcrB of Example 5.

FIGS. 17 to 19 are electron microscope images of *E. coli* AcrB of Example 5. In FIGS. 17 to 19, the analysis substrate was negatively stained and an electron microscope image was captured. In Example 5, compared to Example 4, formation of an aggregate was inhibited because the membrane protein aqueous solution was diluted when the analysis substrate was prepared, and an image which is considered to be a trimer of *E. coli* AcrB could be confirmed. In FIG. 17, the reference numerals F1 and F2 indicate a trimer of *E. coli* AcrB. FIGS. 18 and 19 are partially enlarged views of FIG. 17, FIG. 18 is an enlarged vie of the trimer of the reference numeral F1 and FIG. 19 is an enlarged view of the trimer of the reference numeral F2.

Figure 20:
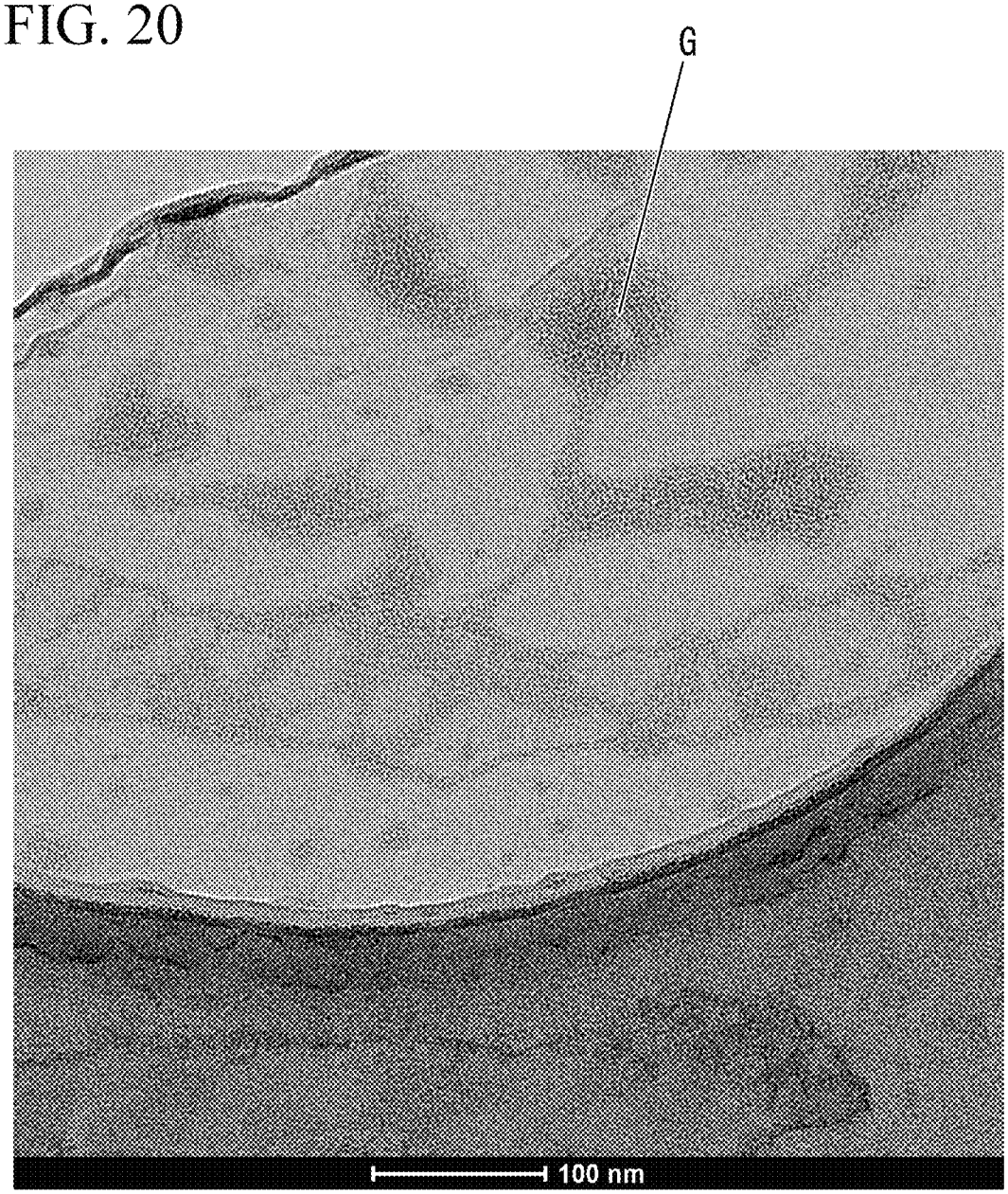
FIG. 20 is an electron microscope image of bacteriorhodopsin of Example 6.

FIG. 20 is an electron microscope image of bacteriorhodopsin of Example 6. In FIG. 20, the analysis substrate was negatively stained and an electron microscope image was captured. It can be understood from FIG. 20 that bacteriorhodopsin formed an aggregate. In FIG. 20, the reference numeral G indicates an aggregate of bacteriorhodopsin.

Figure 21:
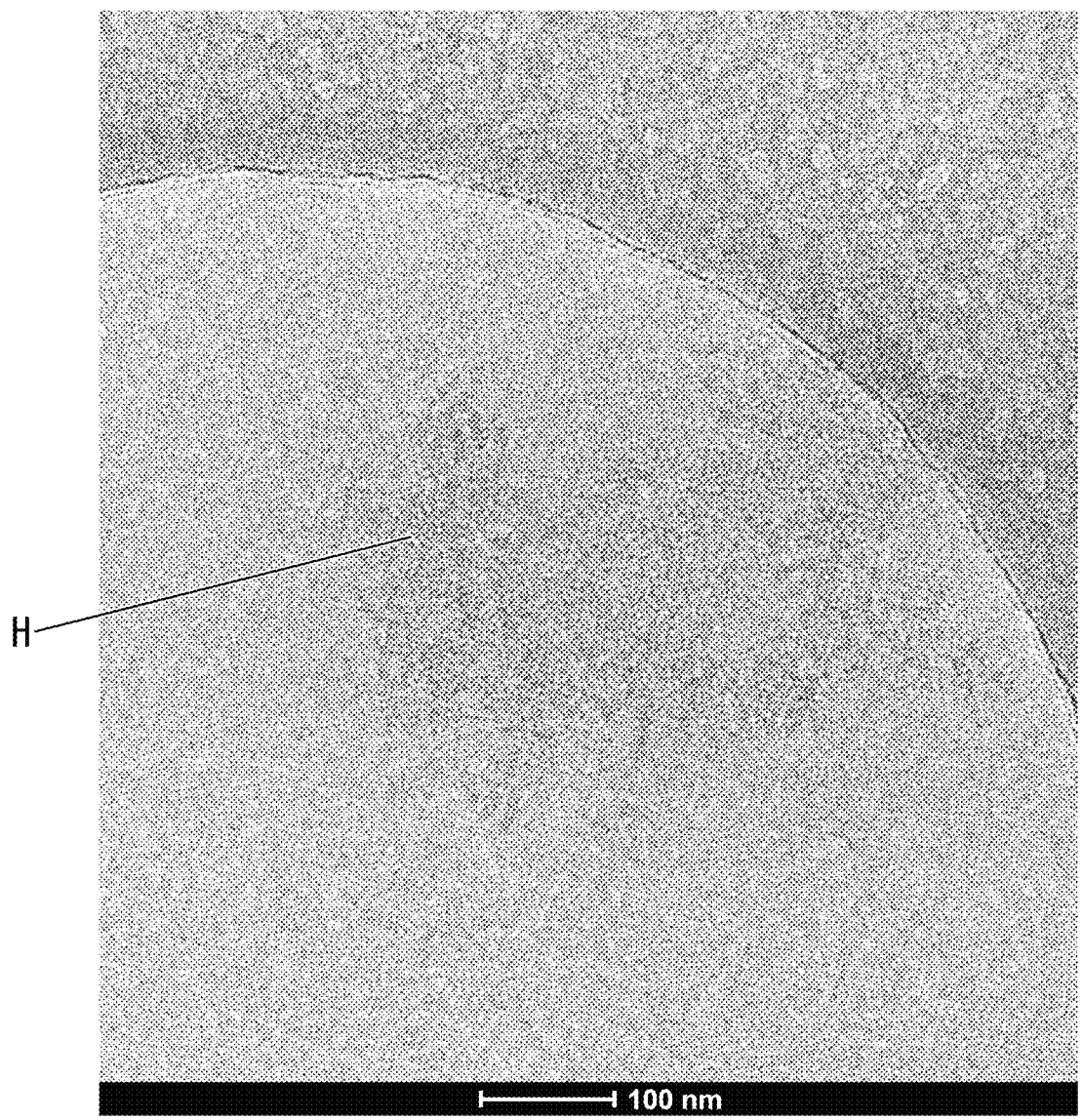
FIG. 21 is an electron microscope image of archaeal AglB proteins of Example 7.

FIG. 21 is an electron microscope image of archaeal AglB proteins of Example 7. In FIG. 21, an electron microscope image was captured by a low-temperature electron microscope method without staining the analysis substrate. It can be understood from FIG. 21 that, when the analysis substrate of the present embodiment was used, an aggregate of membrane proteins could be imaged without staining. In FIG. 21, the reference numeral H indicates an image which is considered to be an aggregate of archaeal AglB proteins.

Figure 22:
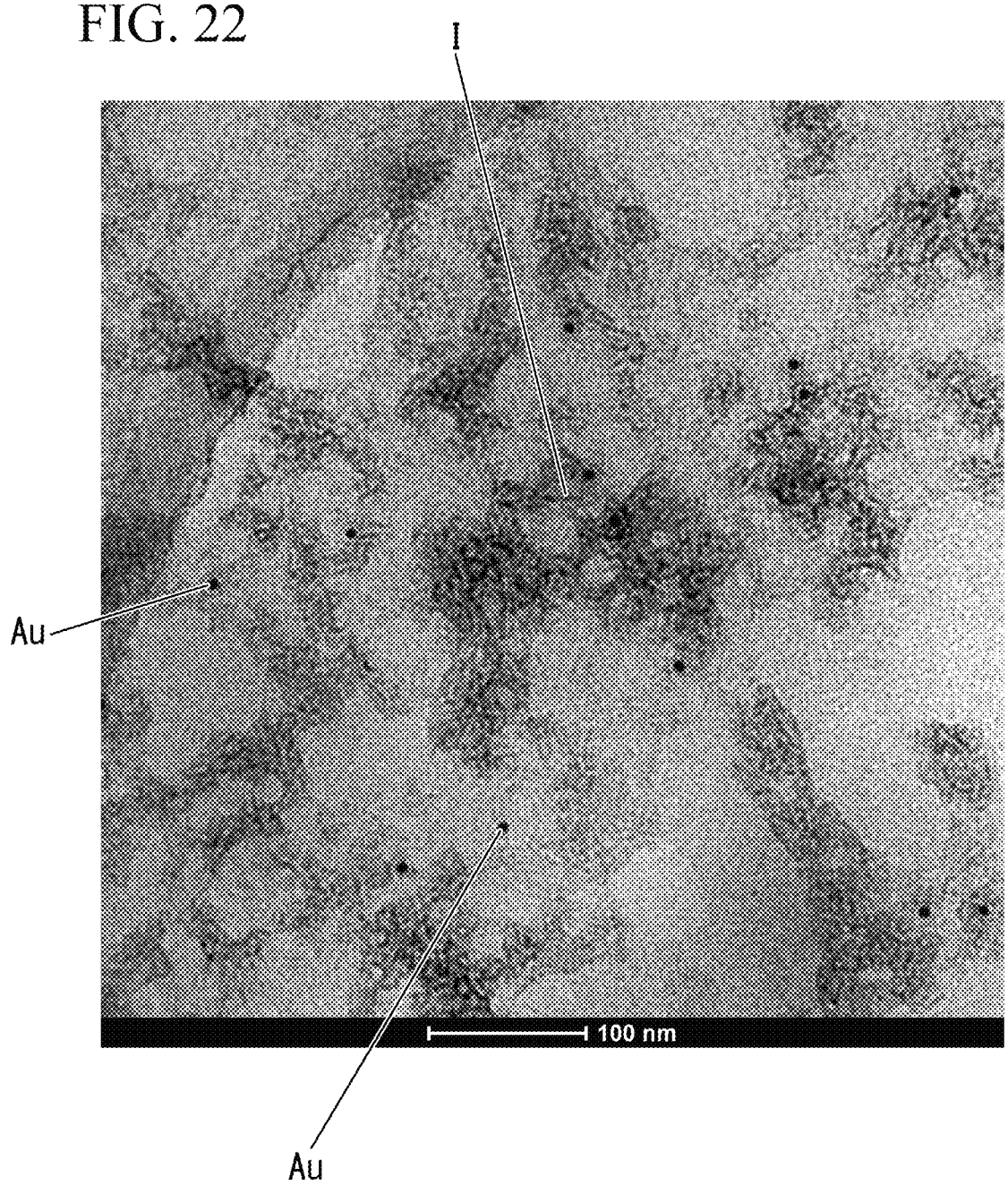
FIG. 22 is an electron microscope image of *E. coli* AcrB proteins of Example 8.

FIG. 22 is an electron microscope image of *E. coli* AcrB proteins of Example 8. In FIG. 22, the reference numeral I indicates an aggregate of *E. coli* AcrB proteins and antibodies. In addition, the points Au appearing in FIG. 22 indicate gold nanoparticles (a diameter of 6 nm).

It can be understood from FIG. 22 that, when the analysis substrate of the present embodiment was used, it was confirmed that the membrane proteins retained in the lipid bilayer membrane were desired membrane proteins according to immunostaining using antibodies labeled with gold nanoparticles or the like.

Based on the above results, it was found that, when membrane proteins were retained in the lipid bilayer membrane according to the present invention, analysis could be performed suitably.

REFERENCE SIGNS LIST 1 to 3 Analysis substrate (membrane protein analysis substrate)
10 Grid (electron microscope grid)
10a First surface
10b Second surface
102a Through-hole
20, 40, 50 Lipid bilayer membrane
30 Membrane protein
21, 22, 41, 42, 51, 52 Lipid monolayer
L1 First lipid
LS1, LS2 Liquid surface
ML1 Monolayer
PS, S3 Solution
S1 First solution
S2 Second solution

What is claimed is:

1. A membrane protein analysis substrate, comprising:
an electron microscope grid having a plurality of through-holes;
a lipid bilayer membrane that is provided to cover at least one of the plurality of through-holes; and
membrane proteins that are retained in a part planarly overlapping positions of the through-holes covered by the lipid bilayer membrane,
wherein the lipid bilayer membrane has a lipid monolayer, and
wherein the lipid monolayer is larger than the through-hole in a plan view, adheres to the electron microscope grid, and constitutes a part of the lipid bilayer membrane.

2. The membrane protein analysis substrate according to claim 1,
wherein one lipid monolayer constituting the lipid bilayer membrane is formed of a first lipid, and
wherein the other lipid monolayer constituting the lipid bilayer membrane is formed of a second lipid different from the first lipid.

3. The membrane protein analysis substrate according to claim 2,
wherein the surface of the electron microscope grid is hydrophobic, wherein one lipid monolayer constituting the lipid bilayer membrane covers a first surface of the electron microscope grid, wherein the other lipid monolayer constituting the lipid bilayer membrane covers a second surface of the electron microscope grid, and wherein the one lipid monolayer and the other lipid monolayer are bonded inside the through-hole, form the lipid bilayer membrane, and cover the through-hole.

4. The membrane protein analysis substrate according to claim 1, wherein the two lipid monolayers constituting the lipid bilayer membrane are formed of the same lipid.

5. The membrane protein analysis substrate according to claim 4, wherein the surface of the electron microscope grid is hydrophobic, wherein one lipid monolayer constituting the lipid bilayer membrane covers one surface of the electron microscope grid, wherein the other lipid monolayer constituting the lipid bilayer membrane is discretely provided inside the plurality of through-holes, and wherein the one lipid monolayer and the other lipid monolayer are bonded inside the through-hole, form the lipid bilayer membrane, and cover the through-hole.

6. The membrane protein analysis substrate according to claim 2 or claim 4, wherein the surface of the electron microscope grid is hydrophilic, and wherein the lipid bilayer membrane covers the through-hole from one surface of the electron microscope grid.

7. A method of analyzing membrane proteins, comprising a process of observing the membrane proteins retained by the membrane protein analysis substrate according to claim 1 under an electron microscope.

8. The method of analyzing membrane proteins according to claim 7, further comprising a process of staining the membrane proteins retained in the lipid bilayer membrane before the process of observing under an electron microscope.

9. The method of analyzing membrane proteins according to claim 7, wherein, in the observing process, the membrane proteins are observed by a low-temperature electron microscope method.

10. A method of forming a lipid bilayer membrane of producing a membrane protein analysis substrate, comprising:

a process of providing a first lipid monolayer on a first surface of an electron microscope grid having a plurality of through-holes;

a process of providing a second lipid monolayer on a second surface of the electron microscope grid and forming a lipid bilayer membrane in which the first lipid monolayer and the second lipid monolayer are bonded; and a process of retaining membrane proteins in the lipid bilayer membrane;

wherein, in the process of providing a first lipid monolayer, the plurality of through-holes are covered from the side of the first surface with the first lipid monolayer, wherein, in the process of forming a lipid bilayer membrane, the plurality of through-holes are covered from the side of the second surface with the second lipid monolayer, and wherein the first lipid monolayer and the second lipid monolayer are bonded inside the plurality of through-holes.

11. The method of producing a membrane protein analysis substrate according to claim 10, wherein the process of providing a first lipid monolayer includes bringing the first surface into contact with the first lipid monolayer formed on a liquid surface of a first solution.

12. The method of producing a membrane protein analysis substrate according to claim 10, wherein the process of providing a second lipid monolayer includes bringing the second surface into contact with the second lipid monolayer formed on a liquid surface of a second solution.

13. The method of producing a membrane protein analysis substrate according to claim 12, wherein, in the process of retaining membrane proteins, the membrane proteins are added to the second solution, and wherein the membrane proteins move from the second solution to the lipid bilayer membrane and are retained in the lipid bilayer membrane.

14. The method of producing a membrane protein analysis substrate according to claim 13, wherein, in the process of retaining membrane proteins, after the membrane proteins solubilized in a buffer solution with a surfactant are added to the second solution, the surfactant adsorbent is added to the second solution, and the surfactant is removed from the second solution.

15. A method of producing a membrane protein analysis substrate, comprising:

a process of bringing one surface of an electron microscope grid having a plurality of through-holes into contact with a lipid monolayer formed on a liquid surface of a solution and forming a lipid bilayer membrane inside the plurality of through-holes; and a process of adding membrane proteins to the solution and retaining the membrane proteins in the lipid bilayer membrane, wherein, in the process of forming a lipid bilayer membrane, the lipid monolayer is transferred to the one surface, and the plurality of through-holes are covered from the side of the one surface with the lipid monolayer, wherein the lipid monolayer forms a self-assembled lipid bilayer membrane inside the plurality of through-holes, and wherein, in the process of retaining membrane proteins, the membrane proteins move from the solution to the lipid bilayer membrane and are retained in the lipid bilayer membrane.

16. The method of producing a membrane protein analysis substrate according to claim 15, wherein, in the process of adding membrane proteins, after the membrane proteins solubilized in a buffer solution with a surfactant are added to the solution, the surfactant adsorbent is added to the solution, and the surfactant is removed from the solution.

17. A method of producing a membrane protein analysis substrate, comprising:

a process of forming a lipid bilayer membrane retaining membrane proteins; and a process of transferring the lipid bilayer membrane retaining the membrane protein to one surface of an electron microscope grid having a plurality of through-holes, wherein, in the process of transferring to one surface, the lipid bilayer membrane is brought into contact with the one surface in such a manner that it covers the entire through-holes.

18. A membrane protein analysis grid, comprising:

an electron microscope grid having a plurality of through-holes; and a lipid bilayer membrane that is provided to cover at least one of the plurality of through-holes, wherein one lipid monolayer constituting the lipid bilayer membrane covers a first surface of the electron microscope grid, wherein the other lipid monolayer constituting the lipid bilayer membrane covers a second surface of the electron microscope grid, and wherein the one lipid monolayer and the other lipid monolayer are bonded inside the through-hole, form the lipid bilayer membrane, and cover the through-hole.

19. The membrane protein analysis grid according to claim 18, wherein one lipid monolayer constituting the lipid bilayer membrane is formed of a first lipid, and wherein the other lipid monolayer constituting the lipid bilayer membrane is formed of a second lipid different from the first lipid.

20. The membrane protein analysis grid according to claim 18, wherein the two lipid monolayers constituting the lipid bilayer membrane are formed of the same lipid.

* * * * *